United States Patent
Galliher et al.

(10) Patent No.: US 12,139,303 B2
(45) Date of Patent: Nov. 12, 2024

(54) METHOD OF FORMING A COLLAPSIBLE BAG USING A MOLD AND MANDREL

(71) Applicant: GLOBAL LIFE SCIENCES SOLUTIONS USA LLC, Marlborough, MA (US)

(72) Inventors: Parrish M. Galliher, Marlborough, MA (US); Geoffrey L. Hodge, Marlborough, MA (US); Michael Fisher, Ashland, MA (US)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 0 days.

(21) Appl. No.: 17/679,511

(22) Filed: Feb. 24, 2022

(65) Prior Publication Data

US 2022/0388725 A1 Dec. 8, 2022

Related U.S. Application Data

(60) Continuation of application No. 16/919,582, filed on Jul. 2, 2020, now Pat. No. 11,312,539, which is a
(Continued)

(51) Int. Cl.
*B65D 33/02* (2006.01)
*B01F 23/23* (2022.01)
(Continued)

(52) U.S. Cl.
CPC ............ *B65D 33/02* (2013.01); *B01F 23/231* (2022.01); *B01F 33/453* (2022.01); *B01F 35/51* (2022.01); *B01F 35/513* (2022.01); *B29C 45/16* (2013.01); *C12M 23/14* (2013.01); *C12M 29/06* (2013.01); *C12M 41/02* (2013.01); *B01F 2101/44* (2022.01); *B29K 2023/0633* (2013.01); *B29L 2031/7128* (2013.01)

(58) Field of Classification Search
CPC ...... B01F 23/231; B01F 33/453; B01F 35/51; B65D 33/02
See application file for complete search history.

(56) References Cited

U.S. PATENT DOCUMENTS 2,985,916 A 3/1957 Reuter et al.
3,722,726 A 3/1973 Du Pont
(Continued)

FOREIGN PATENT DOCUMENTS

CN 1581708 2/2005
DE 02548441 5/1977
(Continued)

OTHER PUBLICATIONS

Mirriam-Webster.com definition of bag, accessed Mar. 31, 2017.
(Continued)

*Primary Examiner* — Robert A Hopkins
(74) *Attorney, Agent, or Firm* — Grogan, Tuccillo & Vanderleeden, LLP

(57) ABSTRACT

A bioreactor configured to contain a volume of liquid is provided. The bioreactor includes a collapsible bag able to contain the volume of liquid, a first sparger connected to the collapsible bag, and a second sparger connected to the collapsible bag.

20 Claims, 8 Drawing Sheets

Related U.S. Application Data continuation of application No. 15/877,795, filed on Jan. 23, 2018, now Pat. No. 11,008,138, which is a continuation of application No. 14/548,371, filed on Nov. 20, 2014, now Pat. No. 9,908,664, which is a division of application No. 13/276,087, filed on Oct. 18, 2011, now Pat. No. 8,894,756, which is a continuation of application No. 11/818,901, filed on Jun. 15, 2007, now abandoned.

(60) Provisional application No. 60/814,647, filed on Jun. 16, 2006.

(51) Int. Cl.
    *B01F 23/231*     (2022.01)
    *B01F 33/45*     (2022.01)
    *B01F 33/453*     (2022.01)
    *B01F 35/51*     (2022.01)
    *B01F 35/513*     (2022.01)
    *B29C 45/16*     (2006.01)
    *C12M 1/00*     (2006.01)
    *C12M 1/21*     (2006.01)
    *B01F 101/44*     (2022.01)
    *B29K 23/00*     (2006.01)
    *B29L 31/00*     (2006.01)

(56) References Cited

U.S. PATENT DOCUMENTS

| | | | |
|---|---|---|---|
| 4,209,259 A | 6/1980 | Rains et al. | |
| 4,310,437 A | 1/1982 | Schreiber | |
| 4,355,906 A | 10/1982 | Ono | |
| 4,624,745 A | 11/1986 | Sande et al. | |
| 4,727,040 A | 2/1988 | Freedman et al. | |
| 4,755,281 A | 7/1988 | Penick | |
| 4,883,759 A | 11/1989 | Hopkins | |
| 4,910,054 A | 3/1990 | Collette et al. | |
| 4,943,404 A | 7/1990 | Waldrop | |
| 4,987,082 A | 1/1991 | Gallagher | |
| 5,075,234 A | 12/1991 | Tunac | |
| 5,935,843 A | 8/1999 | Glendening et al. | |
| 5,985,649 A | 11/1999 | Stensel et al. | |
| 6,465,243 B2 | 10/2002 | Okada et al. | |
| 6,581,802 B1 | 6/2003 | Sperber | |
| 6,630,216 B2 | 10/2003 | Pophusen | |
| 7,384,027 B2 * | 6/2008 | Terentiev | C12M 29/06 435/296.1 |
| 7,635,586 B2 | 12/2009 | West | |
| 8,894,756 B2 | 11/2014 | Galliher et al. | |
| 2002/0076815 A1 | 6/2002 | Banerjee et al. | |
| 2005/0077239 A1 | 4/2005 | Frisch | |
| 2005/0282269 A1* | 12/2005 | Proulx | C12M 29/06 435/296.1 |
| 2006/0033222 A1 | 2/2006 | Godfrey et al. | |
| 2006/0092761 A1 | 5/2006 | Terentiev | |
| 2006/0129026 A1 | 6/2006 | Wallin et al. | |
| 2008/0068920 A1 | 3/2008 | Galliher et al. | |

FOREIGN PATENT DOCUMENTS

| | | | |
|---|---|---|---|
| DE | 278505 | 5/1990 | |
| EP | 0358053 | 3/1990 | |
| EP | 0399972 | 11/1990 | |
| EP | 0530820 | 3/1993 | |
| EP | 829534 A2 * | 3/1998 | ......... B01F 3/04106 |
| EP | 1329201 | 7/2003 | |
| GB | 1181877 | 2/1970 | |
| GB | 2342418 | 4/2000 | |
| JP | 47030619 | 11/1972 | |
| JP | 52030866 | 3/1977 | |
| JP | 63016009 | 1/1988 | |
| JP | 64086867 | 3/1989 | |
| JP | 04024498 | 1/1992 | |
| JP | 474501 | 6/1992 | |
| JP | 05124058 | 2/1993 | |
| JP | 06153902 | 6/1994 | |
| JP | 06238686 | 8/1994 | |
| JP | 09001567 | 1/1997 | |
| JP | 09314596 | 12/1997 | |
| JP | 200251763 | 2/2002 | |
| JP | 2003009843 | 1/2003 | |
| JP | 2004504958 | 2/2004 | |
| WO | 199208743 | 5/1992 | |
| WO | 2002/009924 | 2/2002 | |
| WO | 2005034613 | 4/2005 | |
| WO | 2005068059 | 7/2005 | |
| WO | 2005104706 | 11/2005 | |
| WO | 2005118771 | 12/2005 | |

OTHER PUBLICATIONS

Mirriam-Webster.com definition of collapse, accessed Mar. 21, 2017.

Yusuf Chisti and Murray Moo-Young, Clean-in-place systems for industrial bioreactors: design, validation and operation, 1994, the Macmillan Press Ltd., Journal of Industrial Microbiology, 13, 201-207.

* cited by examiner

METHOD OF FORMING A COLLAPSIBLE BAG USING A MOLD AND MANDREL

CROSS-REFERENCES TO RELATED APPLICATIONS

This application claims priority to and is a continuation of U.S. application Ser. No. 16/919,582, filed on Jul. 2, 2020, which is a continuation of U.S. application Ser. No. 15/877, 795, filed on Jan. 23, 2018 (now U.S. Pat. No. 11,008,138 issued May 18, 2021), which is a continuation of U.S. application Ser. No. 14/548,371, filed on Nov. 20, 2014 (now U.S. Pat. No. 9,908,664 issued Mar. 6, 2018), which is a Divisional of U.S. application Ser. No. 13/276,087, filed Oct. 18, 2011 (now U.S. Pat. No. 8,894,756 issued Nov. 25, 2014), which is a continuation of U.S. application Ser. No. 11/818,901, filed Jun. 15, 2007, which claims the benefit under Title 35, U.S.C. § 119(e) of U.S. Provisional Application Ser. No. 60/814,647, filed Jun. 16, 2006, the disclosures of the foregoing Applications being incorporated herein by reference in their entirety.

FIELD OF INVENTION

The present invention relates generally to systems for containing and manipulating fluids, and in certain embodiments, to systems and methods involving collapsible bags that may be used as reactors for performing chemical, biochemical and/or biological reactions contained therein.

BACKGROUND

A variety of vessels for manipulating fluids and/or for carrying out chemical, biochemical and/or biological reactions are available. For instance, biological materials (e.g., animal and plant cells) including, for example, mammalian, plant or insect cells and microbial cultures can be processed using bioreactors. Traditional bioreactors, which are typically designed as stationary pressurized vessels, or disposable bioreactors, many of which utilize plastic sterile bags, may be used. Although reaction systems and other fluid manipulating systems (e.g., mixing systems) are known, improvements to such systems would be beneficial.

SUMMARY OF THE INVENTION

The present invention relates generally to systems for containing and manipulating fluids, and in certain embodiments, to systems and methods involving supported collapsible bags that may be used as bioreactors for performing chemical, biochemical and/or biological reactions contained therein. The subject matter of the present invention involves, in some cases, interrelated products, alternative solutions to a particular problem, and/or a plurality of different uses of one or more systems and/or articles.

In one aspect of the invention, a series of vessels are provided. In one embodiment, a vessel configured to contain a volume of liquid is provided. The vessel comprises a collapsible bag for containing the volume of liquid, the collapsible bag having a volume of at least 2 liters and a support structure surrounding and containing the collapsible bag. The vessel also includes a first sparger connected to the collapsible bag, the first sparger being in fluid communication with a source of a first gas composition, and a second sparger connected to the collapsible bag, the second sparger being in fluid communication with a source of a second gas composition different from the first gas composition.

In another embodiment, a vessel configured to contain a volume of liquid comprises a collapsible bag able to contain the volume of liquid and a support structure surrounding and containing the collapsible bag. The vessel also includes a first sparger connected to the collapsible bag, the first sparger having a first aperture size, wherein at least a portion of the first sparger is dimensioned to be connected to a source of a first gas, and a second sparger connected to the collapsible bag, the second sparger having a second aperture size, wherein at least a portion of the second sparger is dimensioned to be connected to a source of a second gas.

In another embodiment, a vessel configured to contain a volume of liquid comprises a container able to contain the volume of liquid. The vessel may also include a magnetically-driven antifoaming device, at least a portion of which is positioned in a head space of the container when the container contains the volume of liquid. The antifoaming device is configured and arranged to break up foam in the head space during rotation of at least a portion of the antifoaming device.

In another embodiment, a vessel configured to contain a volume of liquid comprises a collapsible bag able to contain the liquid and a reusable support structure surrounding and containing the collapsible bag. The vessel also comprises a pressure sensor for determining a pressure in the collapsible bag, the pressure sensor in fluid communication with the collapsible bag, and an antifoaming device associated with the collapsible bag and configured to break up foam in the collapsible bag. The vessel may also include a control system operatively associated with the pressure sensor and the antifoaming device, wherein the control system regulates the antifoaming device upon receipt of a signal from the pressure sensor.

In another embodiment, a collapsible bag configured to contain a volume of at least 2 liters is provided. The collapsible bag comprises a first rotatable impeller positioned at a bottom portion of the collapsible bag, the first impeller able to be magnetically rotated, and a second impeller positioned at a top portion of the collapsible bag, the second impeller able to be magnetically rotated.

In another embodiment, a container able to contain a volume of liquid is provided. The container comprises a collapsible bag having a volume of at least 40 liters, wherein the collapsible bag does not include any seams joining two or more flexible wall portions of the collapsible bag, and a reusable support structure surrounding and containing the collapsible bag.

In another aspect of the invention, a series of methods are provided. In one embodiment, a method comprises positioning a rigid component in a mold having a shape configured to mold a container having a volume of at least 10 mL, and introducing a first polymer or polymer precursor into the mold. The method includes forming a seamless container within the mold by solidifying the polymer or polymer precursor to form the container, wherein the component is incorporated in the container.

In another embodiment, a method comprises introducing a first polymer or polymer precursor into a mold, the mold having a shape configured to mold a container having a volume of at least 10 mL, the mold further comprising at least one mandrel for forming a functional component of a liquid containment system. The method also includes forming a container within the mold, forming a component within the mold utilizing the mandrel, and joining the functional component and the container without welding.

In another embodiment, a method comprises introducing a first polymer or polymer precursor into a mold, the mold having a shape configured to mold a collapsible bag having a volume of at least 10 mL and also configured to mold a base including a shaft configured to support a magnetic impeller and forming a collapsible bag within the mold. The method also includes introducing a second polymer precursor into the mold, forming a component of the mixing system by solidifying the second polymer precursor, and joining the component of the mixing system and the collapsible bag without welding.

In another embodiment, an article comprises a collapsible bag comprising a flexible wall portion and a rigid portion comprising a base including a shaft configured to support a magnetic impeller, wherein the rigid portion is embedded with the flexible wall portion.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
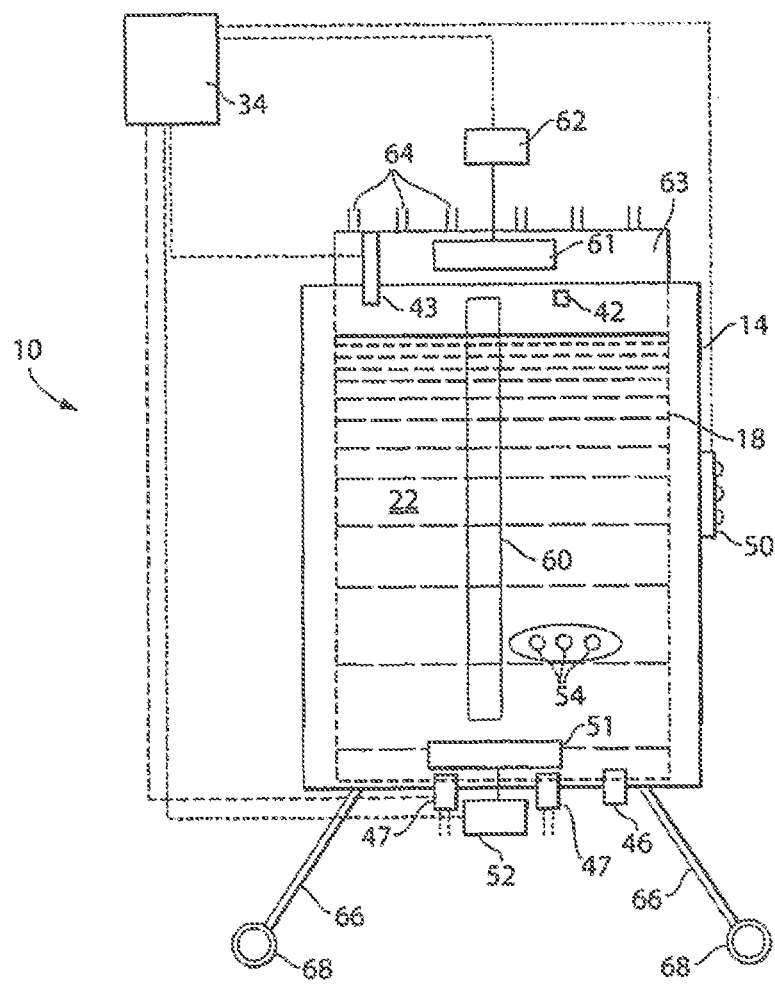
FIG. 1 illustrates one embodiment of the invention, showing a container contained within a support structure.

The present invention relates generally to systems for containing and manipulating fluids, and in certain embodiments, to systems and methods involving collapsible bags that may be used as reactors for performing chemical, biochemical and/or biological reactions contained therein.

Generally, the invention provides a series of improvements and features for fluid containment systems such as gas delivery configurations, foam control systems and bag molding methods and articles for supported collapsible bag vessels and bioreactors. For instance, in one aspect, fluids contained in a vessel can be sparged, e.g., such that a fluid is directed into a container of the vessel, and in some cases, the sparging can be controlled by rapidly activating or altering the degree of sparging as needed. Multiple spargers may be used in some cases. In another aspect, the vessel includes a seamless collapsible bag. In some cases, the collapsible bag may be injected, blown, or spin cast molded. In yet another aspect, the vessel includes a device which can reduce the foam produced or contained within the vessel. Sensors and/or controllers may optionally be used to monitor and/or control foaming.

The following documents are incorporated herein by reference: U.S. Provisional Patent Application Ser. No. 60/903,977, filed Feb. 28, 2007, entitled "Weight Measurements of Liquids in Flexible Containers," by P. A. Mitchell, et al.; U.S. patent application Ser. No. 11/147,124, filed Jun. 6, 2005, entitled "Disposable Bioreactor Systems and Methods," by G. Hodge, et al., published as U.S. Patent Application Publication No. 2005/0272146 on Dec. 8, 2005; International Patent Application No. PCT/US2005/020083, filed Jun. 6, 2005, entitled "Disposable Bioreactor Systems and Methods," by G. Hodge, et al., published as WO 2005/118771 on Dec. 15, 2005; and International Patent Application No. PCT/US2005/002985, filed Feb. 3, 2005, entitled "System and Method for Manufacturing," by G. Hodge, et al., published as WO 2005/076093 on Aug. 18, 2005.

Although much of the description herein involves an exemplary application of the present invention related to bioreactors (and/or biochemical and chemical reaction systems), the invention and its uses are not so limited, and it should be understood that aspects of the invention can also be used in other settings, including those involving containment systems in general, as well as systems for containment and/or processing of a fluid in a container (e.g., mixing systems). It should also be understood that while many examples provided herein involve the use of collapsible bags or flexible containers, aspects of the invention can be integrated with systems involving non-collapsible bags, rigid containers, and other configurations involving liquid containment.

In one aspect, vessels configured to contain a volume of liquid are provided. In certain embodiments, the vessels are a part of a bioreactor system. For example, a non-limiting example of a bioreactor system including a container, such as a flexible container, is shown in the schematic diagram of FIG. 1. As shown in the embodiment illustrated in FIG. 1, vessel 10 includes a reusable support structure 14 (e.g., a stainless steel tank) that surrounds and contains a container 18. In some embodiments, the container is configured as a collapsible bag (e.g., a polymeric bag). Additionally and/or alternatively, all or portions of the collapsible bag or other container may comprise a substantially rigid material such as a rigid polymer, metal, and/or glass. In other embodiments, a rigid container is used in this configuration. The container may be disposable and may be configured to be easily removable from the support structure. In some embodiments, the container is non-integrally connected to the support structure. As used herein, the term "integrally connected," when referring to two or more objects, means separation of the two or more objects requires causing damage to at least one of the object (or components of the object), for example, by breaking or peeling (e.g., separating components fastened together via adhesives, tools, etc.).

If a collapsible bag is used, the collapsible bag may be constructed and arranged for containing a liquid 22, which may contain reactants, media, and/or other components necessary for carrying out a desired process such as a chemical, biochemical and/or biological reaction. The collapsible bag may also be configured such that liquid 22 remains substantially in contact only with the collapsible bag during use and not in contact with support structure 14. In such embodiments, the bag may be disposable and used for a single reaction or a single series of reactions, after which the bag is discarded. Because the liquid in the collapsible bag may not come into contact with the support structure, the support structure can be reused without cleaning. That is, after a reaction takes place in container 18, the container can be removed from the support structure and replaced by a second (e.g., disposable) container. A second reaction can be carried out in the second container without having to clean either the first container or the reusable support structure.

Also shown in FIG. 1 are an optional inlet port 42 and optional outlet port 46, which can be formed in the container and/or reusable support structure and can facilitate more convenient introduction and removal of a liquid and/or gas from the container. The container may have any suitable number of inlet ports and any suitable number of outlet ports. For example, a plurality of inlet ports may be used to provide different gas compositions (e.g., via a plurality of spargers 47), and/or to allow separation of gases prior to their introduction into the container. These ports may be positioned in any suitable location with respect to container 18. For instance, for certain vessels including spargers, the container may include one more gas inlet ports located at a bottom portion of the container. Tubing may be connected to the inlet and/or outlet ports to form, e.g., delivery and harvest lines, respectively, for introducing and removing liquid from the container. Optionally, the container and/or support structure may include a utility tower 50, which may be provided to facilitate interconnection of one or more devices internal to the container and/or support structure with one or more pumps, controllers, and/or electronics (e.g., sensor electronics, electronic interfaces, and pressurized gas controllers) or other devices. Such devices may be controlled using a control system 34.

For systems including multiple spargers, control system 34 may be operatively associated with each of the spargers and configured to operate the spargers independently of each other. This can allow, for example, control of multiple gases being introduced into the container.

The vessel may optionally include a mixing system such as an impeller 51, which can be rotated (e.g., about a single axis) using a motor 52 that can be external to the container. In some embodiments, as described in more detail below, the impeller and motor are magnetically coupled. The mixing system can be controlled by control system 34. Mixing systems are described in further detail below.

Additionally and/or alternatively, the vessel may include an antifoaming system such as a mechanical antifoaming device. As shown in the embodiment illustrated in FIG. 1, an antifoaming device may include, for example, an impeller 61 that can be rotated (e.g., magnetically) using a motor 62, which may be external to the container. The impeller can be used to collapse a foam contained in a head space 63 of the container. In some embodiments, the antifoaming system is in electrical communication with a sensor 43 (e.g., a foam sensor) via control system 34. The sensor may determine, for instance, the level or amount of foam in the head space or the pressure in the container, which can trigger regulation or control of the antifoaming system. In other embodiments, the antifoaming system is operated independently of any sensors.

The support structure and/or the container may also include, in some embodiments, one or more ports 54 that can be used for sampling, analyzing (e.g., determining pH and/or amount of dissolved gases in the liquid), or for other purposes. The support structure may also include one or more site windows 60 for viewing a level of liquid within the container. One or more connections 64 may be positioned at a top portion of the container or at any other suitable location. Connections 64 may include openings, tubes, and/or valves for adding or withdrawing liquids, gases, and the like from the container, each of which may optionally include a flow sensor and/or filter (not shown). The support structure may further include a plurality of legs 66, optionally with wheels 68 for facilitating transport of the vessel.

It should be understood that not all of the features shown in FIG. 1 need be present in all embodiments of the invention and that the illustrated elements may be otherwise positioned or configured. Also, additional elements may be present in other embodiments, such as the elements described herein.

Various aspects of the present invention are directed to a vessel including a container such as a collapsible bag. "Flexible container", "flexible bag", or "collapsible bag" as used herein, indicates that the container or bag is unable to maintain its shape and/or structural integrity when subjected to the internal pressures (e.g., due to the weight and/or hydrostatic pressure of liquids and/or gases contained therein expected during operation) without the benefit of a separate support structure. The collapsible bag may be made out of inherently flexible materials, such as many plastics, or may be made out of what are normally considered rigid materials (e.g., glass or certain metals) but having a thickness and/or physical properties rendering the container as a whole unable to maintain its shape and/or structural integrity when subjected to the internal pressures expected during operation without the benefit of a separate support structure. In some embodiments, collapsible bags include a combination of flexible and rigid materials; for example, the bag may include rigid components such as connections, ports, supports for a mixing and/or antifoaming system, etc.

The container (e.g., collapsible bag) may have any suitable size for containing a liquid. For example, the container may have a volume between 1-40 L, 40-100 L, 100-200 L, 200-300 L, 300-500 L, 500-750 L, 750-1,000 L, 1,000-2,000 L, 2,000-5,000 L, or 5,000-10,000 L. Volumes greater than 10,000 L are also possible.

In some embodiments, the collapsible bag is disposable and is formed of a suitable flexible material. The flexible material may be one that is USP Class VI certified, e.g., silicone, polycarbonate, polyethylene, and polypropylene. Non-limiting examples of flexible materials include polymers such as polyethylene (e.g., linear low density polyethylene and ultra low density polyethylene), polypropylene, polyvinylchloride, polyvinyldichloride, polyvinylidene chloride, ethylene vinyl acetate, polycarbonate, polymethacrylate, polyvinyl alcohol, nylon, silicone rubber, other synthetic rubbers and/or plastics. As noted above, portions of the flexible container may comprise a substantially rigid material such as a rigid polymer (e.g., high density polyethylene), metal, and/or glass (e.g., in areas for supporting fittings, etc.). In other embodiments, the container is substantially rigid material. All or portions of the container may be optically transparent to allow viewing of contents inside the container. The materials or combination of materials used to form the container may be chosen based on one or more properties such as flexibility, puncture strength, tensile strength, liquid and gas permeabilities, opacity, and adaptability to certain processes such as blow molding, injection molding, or spin cast molding (e.g., for forming seamless collapsible bags).

The container (e.g., collapsible bag) may have any suitable thickness for holding a liquid and may be designed to have a certain resistance to puncturing during operation or while being handled. For instance, the walls of a container may have a total thickness of less than or equal to 250 mils (1 mil is 25.4 micrometers), less than or equal to 200 mils, less than or equal to 100 mils, less than or equal to 70 mils (1 mil is 25.4 micrometers), less than or equal to 50 mils, less than or equal to 25 mils, less than or equal to 15 mils, or less than or equal to 10 mils. In some embodiments, the container includes more than one layer of material that may be laminated together or otherwise attached to one another to impart certain properties to the container. For instance, one layer may be formed of a material that is substantially oxygen impermeable. Another layer may be formed of a material to impart strength to the container. Yet another layer may be included to impart chemical resistance to fluid that may be contained in the container. It should be understood that a container may be formed of any suitable combinations of layers and that the invention is not limited in this respect. The container (e.g., collapsible bag) may include, for example, 1 layer, greater than or equal to 2 layers, greater than or equal to 3 layers, or greater than equal to 5 layers of material(s). Each layer may have a thickness of, for example, less than or equal to 200 mils, less than or equal to 100 mils, less than or equal to 50 mils, less than or equal to 25 mils, less than or equal to 15 mils, less than or equal to 10 mils, less than or equal to 5 mils, or less than or equal to 3 mils, or combinations thereof.

In one set of embodiments of the invention, the container is seamless. The container may be, for example, a seamless collapsible bag or a seamless rigid (or semi-rigid) container. Many existing collapsible bags are constructed from two sheets of a plastic material joined by thermal or chemical bonding to form a container having two longitudinal seams. The open ends of the sheets are then sealed using known techniques and access apertures are formed through the container wall. During use, collapsible bags having seams can cause the formation of crevices at or near the seams where fluids or reagents contained therein are not thoroughly mixed. In certain embodiments involving, for example, the use of collapsible bags for performing a chemical, biochemical and/or biological reaction, unmixed reagents can cause a reduction in yield of a desired product. The presence of the seams in a collapsible bag can also result in the inability of the collapsible bag to conform to the shape of a reusable support structure that may support the bag. By using collapsible bags without any seams joining two or more flexible wall portions of the bag, however, the problems of mixing and conformity may be avoided or reduced. In certain embodiments, seamless collapsible bags can be made specifically to fit a particular reusable support structure having a unique shape and configuration. Substantially perfect-fitting collapsible bags can be used, for example, as part of a bioreactor system or a biochemical and/or chemical reaction system. Seamless rigid or semi-rigid containers may also be beneficial in some instances.

In certain embodiments, a collapsible bag that does not include any seams joining two or more flexible wall portions of the collapsible bag (i.e., a seamless collapsible bag) has a certain volume for containing a liquid. The seamless collapsible bag may have a volume of, for example, at least 1 L, at least 10 liters, at least 20 liters, at least 40 liters, at least 50 liters, at least 70 liters, at least 100 liters, at least 150 liters, at least 200 liters, at least 300 liters, at least 500 liters, at least 700 liters, or at least 1,000 liters. Seamless collapsible bags may also have volumes greater than 1,000 liters (e.g., 1,000-5,000 liters or 5,000-10,000 liters) as needed. In some embodiments, the collapsible bag is positioned in a reusable support structure for surrounding and containing the flexible container.

In one embodiment, a seamless collapsible bag is formed in a process in which the bag liner (e.g., the flexible wall portions of the bag), as well as one or more components such as a component of an agitator/mixer system (e.g., a shaft and/or a support base), port, etc. is cast from one continuous supply of a polymeric precursor material. In some cases, the casting may occur without hermetically sealing, e.g., via welding. Such a seamless collapsible bag may allow the interior liquid or other product to contact a generally even surface, e.g., one which does not contain substantial wrinkles, folds, crevices, or the like. In addition, in some cases, the collapsible bag complementarily fits within a support structure when installed and filled with a liquid or product. The seamless collapsible bag may also have a generally uniform polymeric surface chemistry which may, for example, minimize side reactions. Methods of forming seamless collapsible bags involving more than one polymeric precursor materials can also be performed.

Seamless collapsible bags can be created by a variety of methods. In one embodiment, a seamless collapsible bag is formed by injecting liquid plastic into a mold that has been pre-fitted with components such as ports, connections, supports, and rigid portions configured to support a mixing system (e.g., a shaft and/or a base) that are subsequently surrounded, submerged, and/or embedded by the liquid plastic. The component may be a rigid component, e.g., one that can substantially maintain its shape and/or structural integrity during use. Any suitable number of components (e.g., at least 1, 2, 5, 10, 15, etc.) can be integrated with containers (e.g., collapsible bags) using methods described herein. The mold may be designed to form a collapsible bag having the shape and volume of the mold, which may have a substantially similar shape, volume, and/or configuration of a reusable support structure.

In one embodiment, the container is formed by using an embedded component/linear molding (ECM) technique. In one such technique, rigid or pre-made components such as tube ports, agitator bases, etc. are first positioned in the mold. A polymer or polymer precursor used to form a container (e.g., a seamless collapsible bag) may be introduced (e.g., in a melt state) via a polymer fabrication technique such as those described below. In some cases, a component or a portion of the component is partially melted by the polymer precursor, allowing the component to form a continuous element with the container. That is, the component can be joined (e.g., fused) with one or more wall portions of the container (e.g., flexible wall portions of a collapsible bag) to form a single, integral piece of material without seams.

Figure 2A:
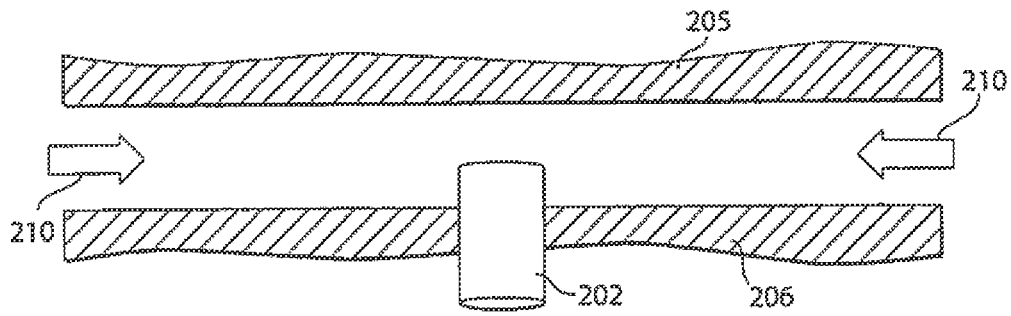
FIGS. 2A-2C illustrate techniques for forming a seamless container, according to another embodiment of the invention.

Referring now to FIG. 2A, an illustrative example of this process is shown. In this figure, a premounted component 202 is held between mold walls 205 and 206. Polymer precursor 210 is then introduced into the mold via any suitable technique. The polymer precursor then flows around component 202 and is hardened, solidified, set, or cured, thereby forming a seamless connection between the polymer itself and the embedded component.

Figure 2B:
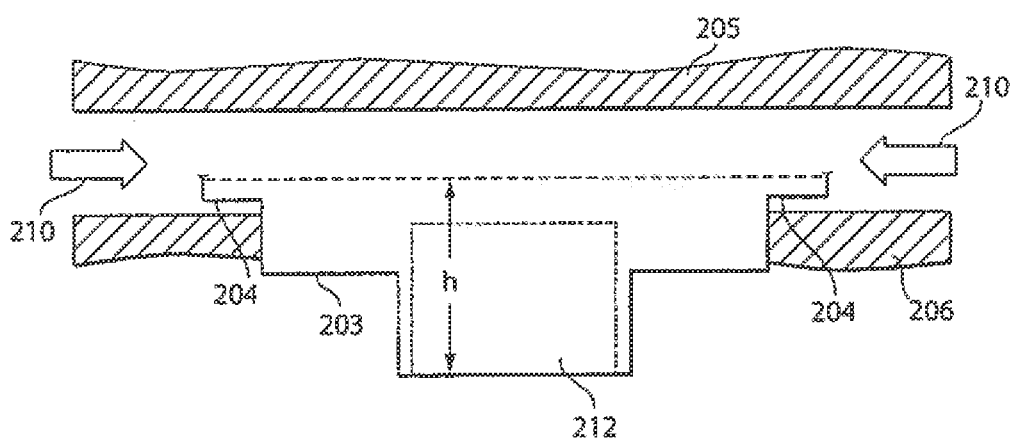

In some cases, components are designed with thinner portions that can be melted with a polymer precursor (e.g., in the melt state) during formation of a container. For example, as shown in the embodiment illustrated in FIG. 2B, component 203, a rigid portion including a recess 212 into which at least a portion of a drive head (not shown) of a mixing and/or antifoaming system can be inserted, is positioned in a mold comprising a shape configured to mold a container. Polymer precursor 210 is then introduced into the mold via any suitable technique. The polymer precursor then flows around component 203 and melts thinner portions 204, causing fusion of portions of the walls of the container and portions of the component. The container and component are then hardened, solidified, set, or cured, thereby forming a single, integral piece of material where a seamless connection exists between the polymer itself and the embedded component. This technique can be used to form, for example, a container (e.g., a seamless collapsible bag) having a volume of greater than, e.g., 40 L, 50 L, 100 L, 200 L, 1,000 L, etc., and having embedded therein components such as one or more support bases and/or shafts for impellers of a mixing system(s).

Accordingly, one embodiment of the invention includes the method of joining together a wall portion of a container and at least a portion of a functional component during formation of the container within a mold, wherein the portion of the functional component is melted during the joining step. The wall portion of the container may have a first thickness and the portion of the functional component may have a second thickness, the thicknesses being within, for example, less than 100%, 80%, 60%, 40%, 20%, 10%, or 5% of each other, relative to the larger of the first and second thicknesses.

Figure 2C:
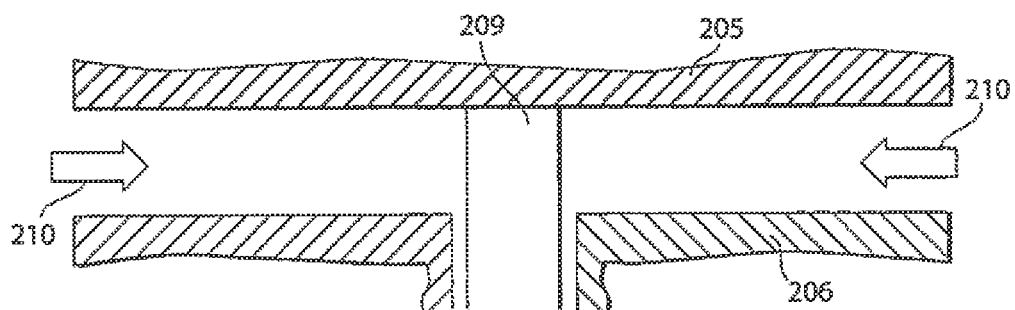

In another embodiment, the container may be formed using a continuous component/liner molding (CCM) technique. In one such technique, a collapsible bag or other container is cast de novo from a polymer or polymer precursor stream. The polymer or polymer precursor used to form the seamless collapsible bag is introduced via a polymer fabrication technique such as those described below. Components can be introduced into the flexible container by using mandrels, barriers, baffles, and the like to direct the polymer precursor to form functional components of a liquid containment system such as tube ports and agitator bases as, for example, one continuous polymer. After setting or curing of the polymer or polymer precursor, the mandrels, barriers, etc., may be withdrawn. For example, as is shown in FIG. 2C, mandrel 209 is held between mold walls 205 and 206. Polymer 210 is then introduced into the mold via any suitable technique, such as those described below. The polymer then flows around mandrel 209 and is hardened or set around the mandrel. The mandrel can then be subsequently withdrawn. This technique can be used to form, for example, a container (e.g., a seamless collapsible bag) having a volume of greater than, e.g., 40 L, 50 L, 100 L, 200 L, 1,000 L, etc., having combined therein components (e.g., rigid components) that are joined to the collapsible bag without welding.

Combinations of these and/or other techniques may also be used in other embodiments. For instance, in some cases, different polymer formulations (such as low molecular weight polyethylene, high molecular weight polyethylene, polypropylene, silicone, polycarbonate, polymethacrylate, combinations thereof or precursors thereof) can be simultaneously injected into regions of the mold designed to form a more rigid structure such as tubing or sensor ports, agitation systems, etc. In one particular embodiment, a method involves introducing a first polymer or polymer precursor into a mold comprising a shape configured to mold a collapsible bag having a volume of at least 10 mL, 1 L, 40 L, 100 L, or 1,000 L, etc. The mold may further comprise a shape configured to mold a component of a mixing and/or antifoaming system such as a shaft and/or base configured to support an impeller. The method may also include introducing a second polymer or polymer precursor into the mold to mold the component of the mixing system. Accordingly, the component of the mixing system and the collapsible bag may be joined without welding using methods described herein. In some instances, the first and second polymers or polymer precursors are introduced simultaneously. The first and second polymers or polymer precursors may be the same in some embodiments, or different in other embodiments. Such a method can be used to form, for example, base plates for mixing/agitation systems, antifoaming systems, or other components. In other embodiments, a number of polymers can be introduced into the mold (e.g., simultaneously) to form containers with multiple components.

As mentioned, a polymer or polymer precursor may be introduced into a mold to form a container such as a collapsible bag (e.g., a seamless collapsible bag) using any suitable technique. For instance, in one embodiment, the collapsible bag may be fabricated via a spin casting process. For example, during spin casting, a mold may be spun during injection of the polymer or polymeric precursor to deposit a uniform coating of plastic on the mold surface. In another embodiment, the collapsible bag is fabricated via an injection molding process. For instance, the polymeric precursor may be pumped into the space between an inner mold and the outer mold. In yet another embodiment, the collapsible bag can be fabricated via a blow molding process. The polymer may be deposited, for example, via a gas injection, to expand the polymer against the mold surface. In yet another embodiment, a combination of these and/or other techniques may be used. Those of ordinary skill in the art will be familiar with polymer processing techniques such as spin casting, injection molding, and/or blow molding, and will be able to use such techniques in the methods of the present invention as described herein to prepare suitable collapsible bags or other containers.

Although many embodiments herein describe seamless collapsible bags, in some embodiments, collapsible bags or other containers described herein can be fabricated with seams between flexible wall portions of the container. In other embodiments, collapsible bags or other containers can be fabricated with seams between a component and one or more flexible wall portions of the container. The act of joining two or more wall portions or a wall portion and a portion of a component may be achieved by methods such as welding (e.g., heat welding and ultrasonic welding), bolting, use of adhesives, fastening, or other attaching techniques. Combination of seams and seamless connections can also be fabricated. It should also be understood that while many of the methods described herein refer to fabrication of collapsible bags, the methods may also be applied to rigid containers. The methods described herein used to form containers such as collapsible bags (e.g., bags with or without seams) may be adapted to include components of various sizes. For instance, although the flexible wall portions of a collapsible bag may having a thickness of, for example, less than or equal to 100 mils, less than or equal to 70 mils, less than or equal to 50 mils, less than or equal to 25 mils, less than or equal to 15 mils, or less than or equal to 10 mils, a component to be incorporated with the container may have a thickness or a height of, for example, greater than 0.5 mm, greater than 1 cm, greater than 1.5 cm, greater than 2 cm, greater than 5 cm, or greater than 10 cm. In some cases, the component has at least one cross-sectional dimension (e.g., a height, length, width, or diameter) of, for example, greater than 0.5 mm, greater than 1 cm, greater than 1.5 cm, greater than 2 cm, greater than 5 cm, greater than 10 cm, greater than 15 cm, greater than 20 cm, greater than 25 cm, or greater than 30 cm. In certain embodiments, the thickness of a collapsible bag (or other container) and the thickness of a portion of a component to be joined (e.g., fused) with the collapsible bag are within 30%, 20%, 15%, 10% or 5% of each other (relative to the thickest portion). This matching of thicknesses can aid joining (e.g., melting, welding, etc.) of the materials, as described in more detail below.

Components that are integrated with collapsible bags or other containers may be formed in any suitable material, which may be the same or a different material from that of the bag or container. For instance, in one embodiment, a container is formed in a first polymer and a component is formed in a second polymer that is different (e.g., having a different composition, molecular weight, and/or chemical structure, etc.) from the first polymer. Those of ordinary skill in the art will be familiar with material processing techniques and will be able to use such techniques in the methods described herein to choose suitable materials and combinations of materials.

In some embodiments, components that are integrated with collapsible bags or other containers using methods described herein are formed in one or more materials that is/are USP Class VI certified, e.g., silicone, polycarbonate, polyethylene, and polypropylene. Non-limiting examples of materials that can be used to form components include polymers such as polyethylene (e.g., low density polyethylene and high density polyethylene), polypropylene, polyvinylchloride, polyvinyldichloride, polyvinylidene chloride, ethylene vinyl acetate, polyvinyl alcohol, polycarbonate, polymethacrylate, nylon, silicone rubber, other synthetic rubbers and/or plastics, and combinations thereof. Ceramics, metals, and magnetic materials can also be used to form all or portions of a component. In some embodiments, all or portions of a component are rigid; in other embodiments, all or portions of a component are flexible.

The material(s) used to form a component may be chosen based on, for example, the function of the component and/or one or more properties such as compatibility with the container, flexibility, tensile strength, hardness, liquid and gas permeabilities, and adaptability to certain processes such as blow molding, injection molding, or spin cast molding.

In certain embodiments, especially in certain embodiments involving fluid manipulations or carrying out a chemical, biochemical and/or biological reaction in a container (e.g., a collapsible bag), the container is substantially closed, e.g., the container is substantially sealed from the environment outside of the container except, in certain embodiments, for one or more inlet and/or outlet ports that allow addition to, and/or withdrawal of contents from, the container. If a collapsible bag is used, it may be substantially deflated prior to being filled with a liquid, and may begin to inflate as it is filled with liquid. In other embodiments, aspects of the invention can be applied to opened container systems.

In some cases, fluids may be introduced and/or removed from a vessel via inlet ports and/or outlet ports. The vessel may be a part of a reactor system for performing a biological, biochemical, or chemical reaction. As mentioned, a container (e.g., a collapsible bag), which may be part of the vessel, may have any suitable number of inlet ports and any suitable number of outlet ports. In some cases, pumps, such as disposable pumps, may be used to introduce a gas or other fluid into the container, e.g., via an inlet port, and/or which may be used to remove a gas or other fluid from the container, e.g., via an outlet port. For instance, a magnetically-coupled pump may be created by encasing a disposable magnetic impeller head in an enclosure with inlet(s) and outlet(s) that achieves fluid pumping. Flexible blades may be used to enhance pumping or provide pressure relief. In another embodiment, pumping of fluids, gas and/or powder may be achieved without pump heads and/or pump chambers by sequentially squeezing, for example, an electromechanical-polymeric tube that effectively achieves "peristalsis". One way valves in the tube may optionally be used, which may aid in the prevention of backflow.

Certain aspects of the present invention also include a support structure, for example, support structure 14 as shown in FIG. 1, which can surround and contain container 18. The support structure may have any suitable shape able to surround and/or contain the container. In some cases, the support structure is reusable. The support structure may be formed of a substantially rigid material. Non-limiting examples of materials that can be used to form the reusable support structure include stainless steel, aluminum, glass, resin-impregnated fiberglass or carbon fiber, polymers (e.g., high-density polyethylene, polyacrylate, polycarbonate, polystyrene, nylon or other polyamides, polyesters, phenolic polymers, and combinations thereof. The materials may be certified for use in the environment in which it is used. For example, non-shedding materials may be used in environments where minimal particulate generation is required.

In some embodiments, the reusable support structure may be designed to have a height and diameter similar to standard stainless steel bioreactors (or other standard reactors or vessels). The design may also be scaleable down to small volume bench reactor systems. Accordingly, the reusable support structure may have any suitable volume for carrying out a desired chemical, biochemical and/or biological reaction. In many instances, the reusable support structure has a volume substantially similar to that of the container. For instance, a single reusable support structure may be used to support and contain and single container having a substantially similar volume. In other cases, however, a reusable support structure is used to contain more than one container. The reusable support structure may have a volume between, for example, 1-100 L, 100-200 L, 200-300 L, 300-500 L, 500-750 L, 750-1,000 L, 1,000-2,000 L, 2,000-5,000 L, or 5,000-10,000 L. Volumes greater than 10,000 L are also possible.

In other embodiments, however a vessel of the present invention does not include a separate container (e.g., collapsible bag) and support structure, but instead comprises a self-supporting disposable container. The container may be, for example, a plastic vessel and, in some cases, may include an agitation system integrally or removably attached thereto. The agitation system may be disposable along with the container. In one particular embodiment, such a system includes an impeller welded or bolted to a polymeric container. It should therefore be understood that many of the aspects and features of the vessels described herein with reference to a container and a support structure (for example, a seamless container, a sparging system, an antifoaming device, etc.), are also applicable to a self-supporting disposable container.

Figure 3:
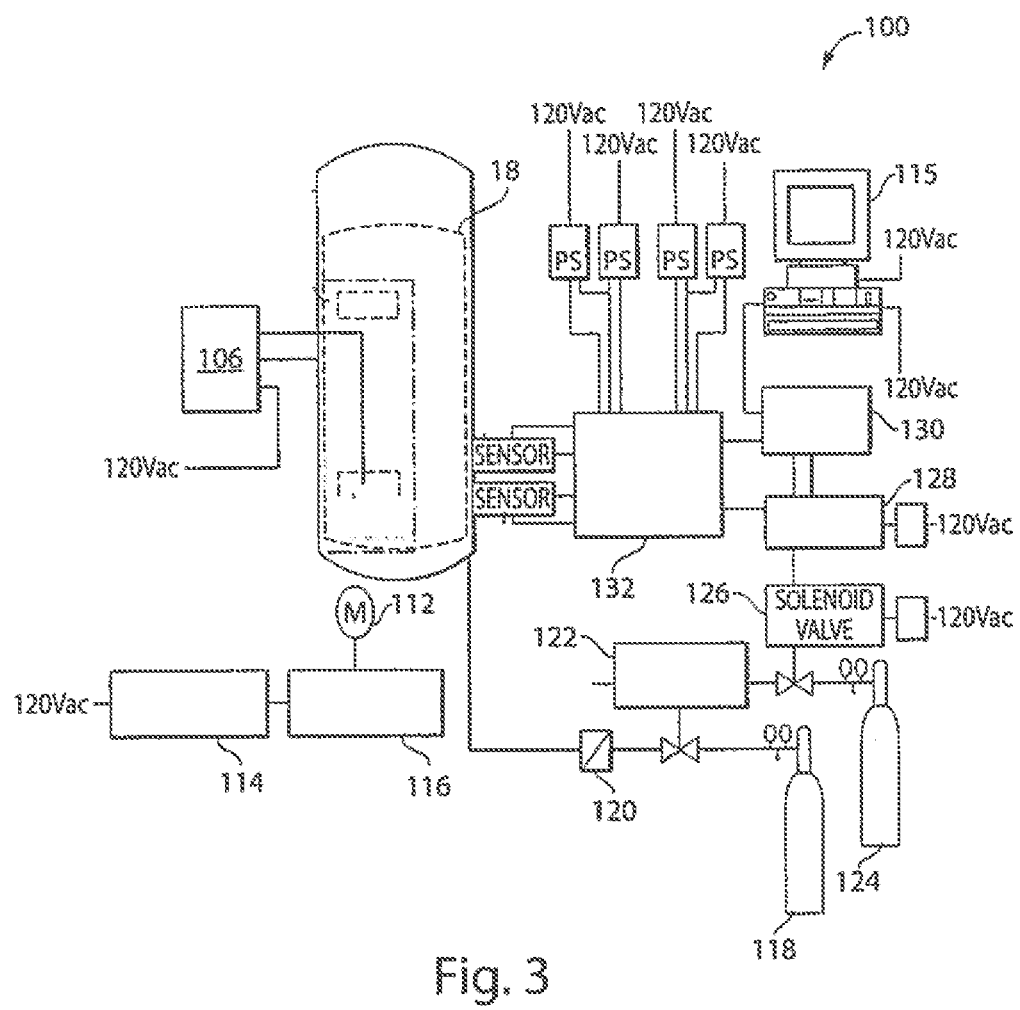
FIG. 3 illustrates a vessel for carrying out fluid manipulations including biological, chemical, and biochemical processes, according to another embodiment of the invention.

As an example, a container, such as container 18 shown in FIG. 3, may include various sensors and/or probes for controlling and/or monitoring one or more process parameters inside the disposable container such as, for example, temperature, pressure, pH, dissolved oxygen (DO), dissolved carbon dioxide (DCO.sub.2), mixing rate, and gas flow rate. The sensor may also be an optical sensor in some cases.

In some embodiments, process control may be achieved in ways which do not compromise the sterile barrier established by a disposable container. For example, gas flow may be monitored and/or controlled by a rotameter or a mass flow meter upstream of an inlet air filter. In another embodiment, disposable optical probes may be designed to use "patches" of material containing an indicator dye which can be mounted on the inner surface of the disposable container and read through the wall of the disposable container via a window in the reusable support structure. For example, dissolved oxygen, pH, and/or CO.sub.2 each may be monitored and controlled by an optical patch and sensor mounted on, e.g., a gamma-irradiatable, biocompatible polymer which, can be sealed to, embedded in, or otherwise attached to the surface of the container.

As a specific example of a sensor, as shown in the embodiment illustrated in FIG. 3, container 18 may be operatively associated with a temperature controller 106 which may be, for example, a heat exchanger, a closed loop water jacket, an electric heating blanket, or a Peltier heater. Other heaters for heating a liquid inside a container are known to those of ordinary skill in the art and can also be used in combination with container 18. The heater may also include a thermocouple and/or a resistance temperature detector (RTD) for sensing a temperature of the contents inside the container. The thermocouple may be operatively connected to the temperature controller to control temperature of the contents in the container. Optionally, a heat-conducting material may be embedded in the surface of the container to provide a heat transfer surface to overcome the insulating effect of the material used to form other portions of the container.

In general, as used herein, a component of an inventive system that is "operatively associated with" one or more other components indicates that such components are directly connected to each other, in direct physical contact with each other without being connected or attached to each other, or are not directly connected to each other or in contact with each other, but are mechanically, electrically (including via electromagnetic signals transmitted through space), or fluidically interconnected so as to cause or enable the components so associated to perform their intended functionality.

Cooling may also be provided by a closed loop water jacket cooling system, a cooling system mounted on the reactor, or by standard heat exchange through a cover/jacket on the reusable support structure (e.g., the heat blanket or a packaged dual unit which provides heating and cooling may a component of a device configured for both heating/cooling but may also be separate from a cooling jacket). Cooling may also to be provided by Peltier coolers. For example, a Peltier cooler may be applied to an exhaust line to condense gas in the exhaust air to help prevent an exhaust filter from wetting out.

In certain embodiments, a reactor system includes gas cooling for cooling the head space and/or exit exhaust. For example, jacket cooling, electrothermal and/or chemical cooling, or a heat exchanger may be provided at an exit air line and/or in the head space of the container. This cooling can enhance condensate return to the container, which can reduce exit air filter plugging and fouling. In some embodiments, purging of pre-cooled gas into the head space can lower the dew point and/or reduce water vapor burden of the exit air gas.

In some cases, sensors and/or probes (e.g., probe 106) may be connected to a sensor electronics module 132, the output of which can be sent to a terminal board 130 and/or a relay box 128. The results of the sensing operations may be input into a computer-implemented control system 115 (e.g., a computer) for calculation and control of various parameters (e.g., temperature and weight/volume measurements) and for display and user interface. Such a control system may also include a combination of electronic, mechanical, and/or pneumatic systems to control heat, air, and/or liquid delivered to or withdrawn from the disposable container as required to stabilize or control the environmental parameters of the process operation. It should be appreciated that the control system may perform other functions and the invention is not limited to having any particular function or set of functions.

The one or more control systems can be implemented in numerous ways, such as with dedicated hardware and/or firmware, using a processor that is programmed using microcode or software to perform the functions recited above or any suitable combination of the foregoing. A control system may control one or more operations of a single reactor for a biological, biochemical or chemical reaction, or of multiple (separate or interconnected) reactors.

Each of systems described herein (e.g., with reference to FIG. 3), and components thereof, may be implemented using any of a variety of technologies, including software (e.g., C, C#, C++, Java, or a combination thereof), hardware (e.g., one or more application-specific integrated circuits), firmware (e.g., electrically-programmed memory) or any combination thereof.

Various embodiments according to the invention may be implemented on one or more computer systems. These computer systems, may be, for example, general-purpose computers such as those based on Intel PENTIUM-type and XScale-type processors, Motorola PowerPC, Motorola DragonBall, IBM HPC, Sun UltraSPARC, Hewlett-Packard PA-RISC processors, any of a variety of processors available from Advanced Micro Devices (AMD) or any other type of processor. It should be appreciated that one or more of any type of computer system may be used to implement various embodiments of the invention. The computer system may include specially-programmed, special-purpose hardware, for example, an application-specific integrated circuit (ASIC). Aspects of the invention may be implemented in software, hardware or firmware, or any combination thereof. Further, such methods, acts, systems, system elements and components thereof may be implemented as part of the computer system described above or as an independent component.

In one embodiment, a control system operatively associated with a vessel described herein is portable. The control system may include, for example, all or many of the necessary controls and functions required to perform a fluidic manipulation (e.g., mixing and reactions) in the control system. The control system may include a support and wheels for facilitating transport of the vessel. Advantageously, such a portable control system can be programmed with set instructions, if desired, transported (optionally with the vessel), and hooked up to a vessel, ready to perform a fluid manipulation in a shorter amount of time than conventional fluid manipulation control systems (e.g., less than 1 week, 3 days, 1 day, 12 hours, 6 hours, 3 hours, or even less than 1 hour).

A vessel, including the container, may also be connected to one or more sources of gases such as air, oxygen, carbon dioxide, nitrogen, ammonia, or mixtures thereof, in various aspects of the invention. The gases may be compressed, pumped, etc. Such gases may be used to provide suitable growth and/or reaction conditions for producing a product inside the container. The gases may also be used to provide sparging to the contents inside the container, e.g., for mixing or other purposes. For instance, in certain embodiments employing spargers, bubble size and distribution can be controlled by passing an inlet gas stream through a porous surface prior to being added to the container. Additionally, the sparging surface may be used as a cell separation device by alternating pressurization and depressurization (or application of vacuum) on the exterior surface of the porous surface, or by any other suitable method.

As a specific example, FIG. 3 shows various sources of gases 118 and 124. The inlet gases may optionally pass through filter 120 and/or a flow meter and/or valve 122, which may be controlled by controller system 115, prior to entering the container. Valve 122 may be a pneumatic actuator (actuated by, e.g., compressed air/carbon dioxide or other gas 124), which may be controlled by a solenoid valve 126. These solenoid valves may be controlled by a relay 128 connected to terminal board 130, which is connected to the controller system 115. The terminal board may comprise, for example, a PCI terminal board, or a USB/parallel, or fire port terminal board of connection. In other embodiments, flush closing valves can be used for addition ports, harvest and sampling valves. Progressive tubing pinch valves that are able to meter flow accurately can also be used. In some cases, the valves may be flush closing valves (e.g., for inlet ports, outlet ports, sampling ports, etc.). The inlet gases may be connected to any suitable inlet of the vessel. In one embodiment, the inlet gases are associated with one or more spargers which can be controlled independently, as described in more detail below.

As shown in the exemplary embodiment illustrated in FIG. 3, the container and support structure illustrated in FIG. 1 can be operatively associated with a variety of components as part of an overall bioreactor system 100, according to another aspect of the invention. Accordingly, the container and/or support structure may include several fittings to facilitate connection to functional component such as filters, sensors, and mixers, as well as connections to lines for providing reagents such as liquid media, gases, and the like. The container and the fittings may be sterilized prior to use so as to provide a "sterile envelope" protecting the contents inside the container from airborne contaminants outside. In some embodiments, the contents inside the container do not contact the reusable support structure and, therefore, the reusable support structure can be reused after carrying out a particular chemical, biochemical and/or biological reaction without being sterilized, while the container and/or fittings connected to the container can be discarded. In other embodiments, the container, fittings, and/or reusable support structure may be reused (e.g., after cleaning and sterilization).

A vessel may also include a mixing system for mixing contents of the container, in another aspect. In some cases, more than one agitator or mixer may be used, and the agitators and/or mixes may the same or different. More than one agitation system may be used, for example, to increase mixing power. In some cases, the agitator may be one in which the height can be adjusted, e.g., such that the draft shaft allows raising of an impeller or agitator above the bottom of the tank and/or allows for multiple impellers or agitators to be used. A mixing system of a vessel may be disposable or intended for a single use (e.g., along with the container), in some cases.

Various methods for mixing fluids can be implemented in the container. For instance, mixers based on magnetic actuation, sparging, and/or air-lift can be used. Direct shaft-drive mixers that are sealed and not magnetically coupled can also be used. In one particular embodiment, mixing systems such as the ones disclosed in U.S. patent application Ser. No. 11/147,124, filed Jun. 6, 2005, entitled "Disposable Bioreactor Systems and Methods," by G. Hodge, et al., published as U.S. Patent Application Publication No. 2005/0272146 on Dec. 8, 2005, which is incorporated herein by reference in its entirety, are used with embodiments described herein. For example, the mixing system may include a motor 112, e.g., for driving an impeller (or other component used for mixing) positioned inside the container, a power conditioner 114, and/or a motor controller 116.

In some cases, a plurality (e.g., more than 1, 2, or 3, etc.) of mixers or impellers are used for mixing contents in a container. Additionally and/or alternatively, a mixing system may include an adjustable height impeller and/or an impeller with varying impeller blade configurations. For instance, the mixer may have an extended drive shaft which allows the impeller to be raised to different heights relative to the bottom of the container. The extended shaft can also allow integration of multiple impellers. In another embodiment, a bioreactor system includes more than one agitation drive per container, which can increase mixing power.

To enhance mixing efficiency, the container may include baffles such as internal film webs or protrusions, e.g., positioned across the inside of the container or extending from the inner surface of the container at different heights and at various angles. The baffles may be formed of in any suitable material such as a polymer, a metal, or a ceramic so long as they can be integrated with the container.

In one embodiment, a direct drive agitator is used. Typically, the agitator includes a direct shaft drive that is inserted into the container. In certain instances, the location where the shaft exits the container may be maintained in a sterile condition. For instance, internal and/or external rotating seals may be used to maintain a sterile seal, and/or live hot steam may be used to facilitate maintenance of the sterile seal. By maintaining such a sterile seal, contamination caused by the shaft, e.g., from the external environment, from the exiting gases, etc., may be reduced or avoided.

In another embodiment, a magnetic agitator is used. Typically, a magnetic agitator uses magnets such as fixed or permanent magnets to rotate or otherwise move the agitator, for example, impellers, blades, vanes, plates, cones, etc. In some cases, the magnets within the magnetic agitator are stationary and can be turned on or activated in sequence to accelerate or decelerate the agitator, e.g., via an inner magnetic impeller hub. As there is no penetration of the container by a shaft, there may be no need to maintain the agitator in a sterile condition, e.g., using internal and/or external rotating seals, live hot steam, or the like.

In yet another embodiment, an electromechanical polymeric agitator is used, e.g., an agitator that includes an electromechanical polymer-based impeller that spins itself by "paddling," i.e., where the agitator is mechanically flapped to propel the agitator or impeller, e.g., rotationally.

Specific non-limiting examples of devices that can be used as a mixing system, and/or an antifoaming system in certain embodiments, are illustrated in FIGS. 4A-8. The devices shown include a magnetically-actuated impeller, although other arrangements are possible. In some of these magnetic configurations, the motor is not directly connected to the impeller. Magnets associated with a drive head can be aligned with magnets associated with an impeller hub, such that the drive head can rotate the impeller through magnetic interactions. In some cases, the motor portion (and other motor associated components) may be mounted on the support structure.

Figure 4A:
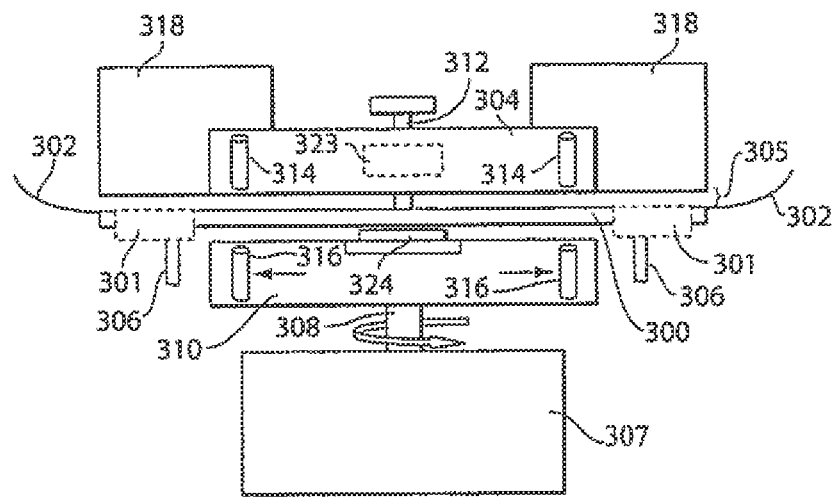
FIGS. 4A-4B illustrate various devices including impellers, according to another embodiment of the invention.

As shown in FIG. 4A, this exemplary system generally includes an impeller support 300 affixed to portions of a container wall 302, preferably at a lower portion thereof, an impeller hub 304, a motor 306, a motor shaft 308 and a drive head 310. The impeller support may be affixed to the wall of the container using any suitable technique, e.g., by heat welding together two portions of a two-piece impeller support, sandwiching the container wall therebetween or onto the wall, or using other methods described herein. As one example, an opening in the wall of the container may be used to allow a central portion of the impeller plate to extend from an exterior of the container to the interior (or vise versa). Then a sealing ring (not shown) may be adhered or the container may be welded directly to an outer circumference of the impeller support to seal the container wall therebetween. As another example, an undersized opening in the wall of the container may be used to form a seal with a circumferential edge of the impeller support slightly larger than the opening. In other embodiments, at least a portion of the impeller support is embedded with a wall of the container and/or the impeller support and container are fabricated simultaneously (e.g., by spin casting, injection molding, or blow molding).

One feature according to one embodiment of the invention is directed to the inclusion of one or more spargers associated with an impeller support, which may be used to direct air or other gases into the container. In some cases, the sparger may include porous, micro-porous, or ultrafiltration elements 301 (e.g., sparging elements). The spargers may be used to allow a gaseous sparge or fluids into and/or out of the container by being dimensioned for connection to a source of a gas; this connection may take place via tubing 307. Such sparging and/or fluid addition or removal may be used, in some cases, in conjunction with a mixing system (e.g., the rotation of the impeller hub). Sparging systems are described in more detail below.

In the embodiment illustrated in FIG. 4A, the interior side of the impeller support may include a shaft or post 312 to which a central opening in the impeller hub 304 receives. The impeller hub may be maintained at a slight distance 305 above the surface of the impeller support (e.g., using a physical spacer) to prevent friction therebetween. Low friction materials may be used in the manufacture of the impeller hub to minimize friction between the impeller hub and the post. In another embodiment, one or more bearings may be included to reduce friction. For instance, the impeller hub may include, in certain instances, a bearing 323 (e.g., a roller bearing, ball bearing (e.g., a radial axis ball bearing), thrust bearing, race bearing, double raceway bearing, lazy-susan bearing, or any other suitable bearing) for reducing or preventing friction between the impeller support and the post. Additionally, the drive head may include a physical spacer 324 for reducing or preventing friction between the drive head and the impeller support.

The impeller hub also may include one or more magnets 314, which may be positioned at a periphery of the hub or any other suitable position, and may correspond to a position of a magnet(s) 316 provided on the drive head 310. The poles of the magnets may be aligned in a manner that increases the amount of magnetic attraction between the magnets of the impeller hub and those of the drive head.

The drive head 310 may be centrally mounted on a shaft 308 of motor 306. The impeller hub also may include one or more impeller blades 318. In some cases, the embedded magnet(s) in the impeller can also be used to remove ferrous or magnetic particles from solutions, slurries, or powders.

An example of such a system is described in more detail in U.S. patent application Ser. No. 11/147,124, filed Jun. 6, 2005, entitled "Disposable Bioreactor Systems and Methods," by G. Hodge, et al., published as U.S. Patent Application Publication No. 2005/0272146 on Dec. 8, 2005, incorporated herein by reference.

Figure 4B:
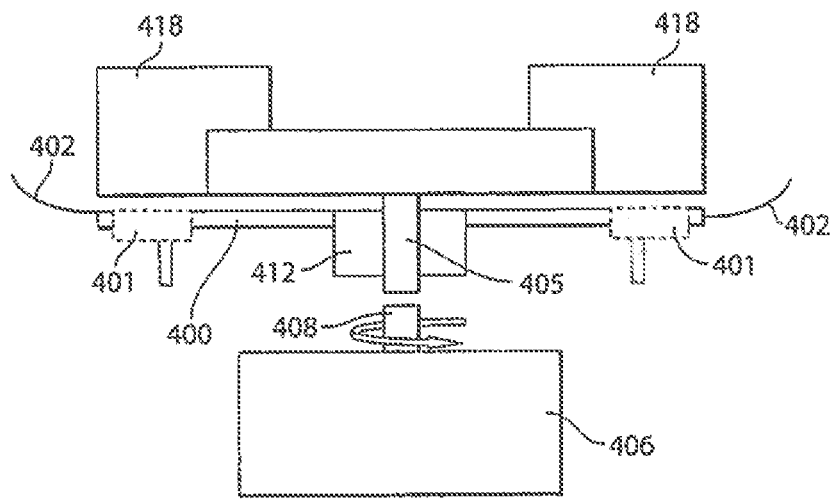

FIG. 4B illustrates another embodiment, having a mechanically-driven impeller. As shown, this embodiment generally includes an impeller support 400, an impeller hub 404 with shaft 405, and an external motor 406 with shaft 408. The connection of shafts between the impeller hub shaft and the motor shaft may be accomplished in a matter familiar to one of ordinary skill in the art (e.g., gear box, hex drive, or the like).

The impeller support can be affixed, for instance, to a side of the bioreactor wall 402 at a lower portion thereof. The impeller support may be affixed to the wall of the bioreactor by any of the methods discussed herein. Porous, microporous, or ultrafiltration elements 401 may also be included in the present embodiment to allow gaseous sparge or fluids into and out of the bioreactor, as discussed in detail below. In the embodiment illustrated in FIG. 4B, the shaft of the impeller hub may be received in a seal 412 (which may also include a bearing, in some cases) centrally located in an impeller support 400. The seal can be used to insure that the contents of the container are not contaminated. The impeller hub can also be maintained at a slight distance above the surface of the impeller support to prevent friction therebetween. The impeller hub may include one or more impeller blades 418, or other suitable mixing structures, such as vanes, plates, cones, etc.

One aspect of the invention involves the recognition that a careful and close alignment, vertically and horizontally, between the drive head and impeller support can add significant benefits to devices of the invention. Prior to the invention, this may not have been recognized or appreciated as indicated by the general acceptance of the utility, and potential lack of need for improvement, of typical magnetic stirring/rotating mechanisms for fluids. An example includes traditional magnetic stir bar arrangements in chemical and biochemical laboratories, where it is typically quite acceptable for magnetic stirrer motors, and stir bars located within a reaction flask, to be not carefully aligned or carefully positioned in proximity to each other. The present invention involves recognition that better positioning and proximity can be achieved through techniques of the invention and result in better potential stirring torque and/or stirring rotational rates.

Figure 5:
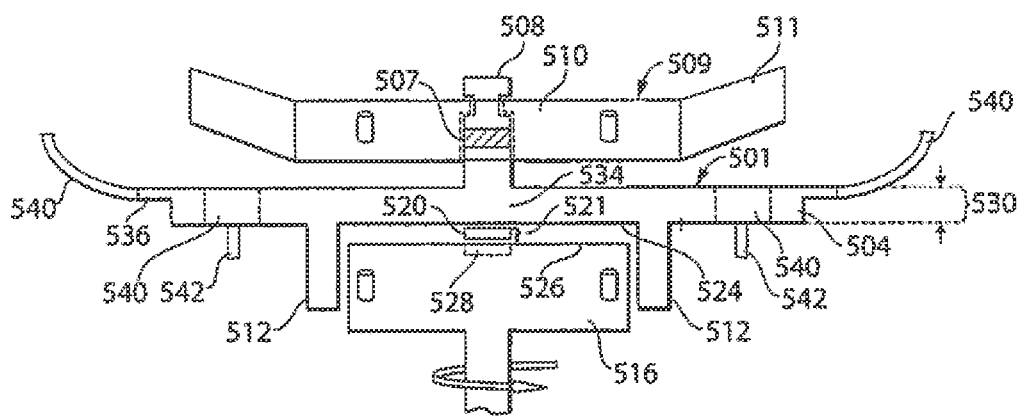
FIG. 5 shows an impeller magnetically coupled to an external motor, according to another embodiment of the invention.

Referring now to FIG. 5, one embodiment of a drive head magnetically coupled to an impeller of the invention is illustrated schematically. In FIG. 5, an impeller support 501, shown in a cross-section, includes a substantially horizontal portion 504, from which a substantially vertical impeller shaft 508 extends upwardly supporting an impeller 509 (which may include a core 510 and blades 511). Impeller 509 may rotate about shaft 508. Optionally, this rotation may be facilitated by a bearing 507, which may be any suitable bearing such as a roller bearing, ball bearing (e.g., a radial axis ball bearing), thrust bearing, race bearing, double raceway bearing, lazy-susan bearing, or the like. Impeller support 501 includes drive head alignment elements 512 which, in the embodiment illustrated, are substantially vertical downwardly-depending ridges which can define a circular recess into which at least a portion of a drive head 516 can be inserted. Guide elements 512 are positioned such that drive head, when engaged with the impeller support, position the drive head at a predetermined desired location relative impeller 509. In one arrangement, guide elements 512 center the drive head, when engaged with the impeller support, with respect to impeller 509. As a further, optional embodiment, a physical spacer 520 can be provided between drive head 516 and a bottom surface 524 of the impeller support aligned with that portion of the top surface 526 of the drive head at the location at which the drive head is ideally positioned with respect to the impeller support. Physical spacer 520 physically separates, by a desired distance, the bottom surface 524 of the impeller support with a top surface 526 of the drive head, but, at least one portion between the top surface of the drive head and bottom surface of the impeller support, may define a continuous, physical connection (free of voids of air or the like), between the drive head and the impeller support. This allows for closer tolerance of the drive head with the impeller support than would have been realized in many prior arrangements, and it allows for reproducible and secure engagement of the drive head with the impeller support. In some cases, the drive head includes a recess 528 into which at least a portion of physical spacer 520 can be inserted. This arrangement can allow reproducible and secure engagement of the drive head with to the physical spacer.

The bottom of the impeller support and the top surface of the drive head can be separated (e.g., using a physical spacer) by a distance 521. In one embodiment, distance 521 is no greater than 50% of average thickness 530 of the substantially horizontal portion 504 of the impeller support. In other embodiments, this distance is no more than 40%, 30%, 20%, 10%, or 5% of the thickness of the impeller support.

In some embodiments, physical spacer 520 has a thickness no greater than 50% of average thickness 530 of the substantially horizontal portion 504 of the impeller support. In other embodiments, this thickness is no more than 40%, 30%, 20%, 10%, or 5% of the thickness of the impeller support.

In one set of embodiments, physical spacer 520 is a bearing that facilitates rotation of the drive head relative to the impeller support. Where physical spacer 520 is a bearing, any suitable bearing can be selected such as a roller bearing, ball bearing (e.g., a radial axis ball bearing), thrust bearing, race bearing, double raceway bearing, lazy-susan bearing, or the like.

In the embodiment illustrated in FIG. 5, the drive head can vary in position, relative to shaft 508, horizontally no more than 5 mm during normal operation or, in other embodiments, no more than 4, 3, 2, 1 (0.5, or 0.25 mm during normal operation). The drive head can also vary in distance relative to bottom surface 524 of the impeller support by no more than 10 mm, 1 mm, 0.5 mm, 0.25 mm, 0.1 mm, or 0.005 mm in certain embodiments with the use of the arrangements illustrated in FIG. 5.

The arrangements of FIG. 5, especially in embodiments where physical spacer 520 is used, also adds physical support to impeller support 501 in addition to any other physical support which the impeller support 501 might receive. This added support is particularly advantageous in collapsible bag arrangements including impellers (e.g., for mixers and/or antifoaming devices).

Optionally, impeller support 501 may include spargers 540 positioned beneath blades of the impeller. The spargers can be dimensioned for connection to one or more sources of gas. For example, the spargers may include a port that can be connected to tubing 542 in fluid communication with one or more sources of gas.

Although many of the figures described herein show impellers that are positioned at or near a bottom portion of a container, in other embodiments, impellers can be positioned at any suitable location within a container, for example, near the center or a top portion of a container. This can be achieved by extending the length of a shaft which supports the impeller, or by any other suitable configuration. Positions of impellers in a container may depend on the process to be performed in the container. For instance, in some embodiments where sparging is required, impellers may be positioned near the sparger such that the impeller can sweep and/or regulate the bubbles introduced into the container. Additionally, although the figures described herein show a single impeller associated with a shaft, more than one impeller can be used in some instances. For example, a first impeller coupled to a shaft may be located near a bottom portion of the container and a second impeller coupled to the shaft may be positioned near the center of the container. The first impeller may provide adequate sweeping of a sparged gas, and the second impeller may provide adequate mixing of contents within the container.

In one aspect of the invention, the impeller support is uniquely designed to be readily fastenable to a collapsible bag. Certain know arrangements of impellers attached to collapsible bags may suffer from drawbacks resulting from non-ideal attachment of the bag to the impeller support, or non-ideal techniques for such attachment, or both. As shown in the embodiment illustrated in FIG. 5, the present invention, in this aspect, includes an impeller support having a base, substantially perpendicular to a shaft upon which the impeller rotates, having a first portion 534 of average thickness sufficient to adequately support the impeller shaft, and a second, peripheral portion 536 thinner than the first portion for facilitating attachment to the bag. The first portion thickness is defined as the overall thickness cross-section taken up by the first portion at any point and, where the first portion includes a ribbed or other structure including various thicknesses, the thickness for purposes of this discussion is defined as the thickest portion. The second, peripheral portion, in one embodiment, defines a composition similar to or essentially identical to that of the collapsible bag, and is provided in a thickness similar to that of the collapsible bag. In other embodiments, the second, peripheral portion is formed by a composition different than that of the collapsible bag. For instance, in some embodiments, the first portion is formed in low density polyethylene, and the second portion is formed in high density polyethylene, polypropylene, silicone, polycarbonate, and/or polymethacrylate.

The thickness of the peripheral portion of the support and the thickness of the walls of collapsible bag 540, prior to attachment, may differ by no more than 100%, or by no more than 80%, 60%, 40%, 20%, or 10% in other embodiments (e.g., as a percentage of the greater thickness between the walls of the bag and the peripheral portion). This aspect of the invention involves, in part, the discovery that where the thickness of the peripheral portion of the impeller support and the thickness of the disposable bag (at least the portion attachable to the impeller support) are made of similar (or compatible) materials and are of similar thickness, then joining of one to the other can be facilitated easily, reproducibly, and with a product that is free of significant irregularity and thickness in the transition of the bag to the impeller support attachment portion. Thus, one aspect of the invention involves the product of attachment of a collapsible bag and an impeller support each as defined above, and in another aspect involves a kit including an impeller support and a collapsible bag prior to attachment. As described herein, joining of the bag and the support can be performed by any suitable method including, for example, molding (e.g., as described above in connection with FIGS. 2A-2C) and welding (e.g., ultrasonic or heat welding).

Figure 6:
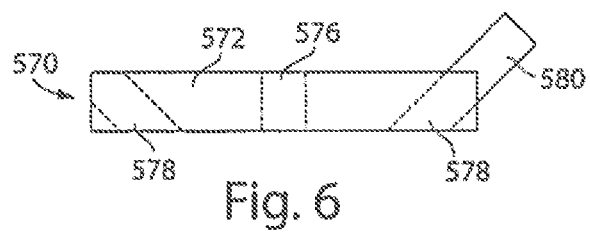
FIG. 6 shows an impeller, according to another embodiment of the invention.

Another aspect of the invention involves impellers with replaceable blades. FIG. 6 illustrates an impeller 570 according to one embodiment of this aspect of the invention which includes a hub 572 which can have a generally circular outer perimeter and may include a center passage 576 before within which the impeller shaft or post (not illustrated) resides. Hub 572 includes one or more slots 578 within which one or more impeller blades 580 can, in some embodiments, be replaceably inserted. As illustrated, one slot 578 is shown not containing a blade and one slot 578 is shown containing an impeller blade. The blade and blade slots are illustrated very schematically and, of course, those of ordinary skill in the art will recognize that a variety of different sizes, shapes, and pitches of blades and slots can be selected by those of ordinary skill in the art for a variety of mixing purposes described herein and known in the art. Blades 580 can be positioned and held within slots 578 securely enough for suitable use and accordance with the invention by any number of techniques including, for example, friction fitting, press fitting, detent mechanism, a clipping and clip release arrangement, fastening with screws, pegs, clamps, or the like, welding (e.g., heat and ultrasonic welding), and use of adhesives.

The replaceable blade arrangement of the invention as illustrated in FIG. 6 provides the advantage in that different blades can be used with a single hub in a mixing/rotating arrangement so that the arrangement can be used for different purposes or involving different rotational speed, torque, mixing profile, or the like. For example, blades of a first size or pitch can be replaced with blades of a second size or pitch to create greater or lesser sheer, aeration, mixing or the like as would be understood by those of ordinary skill in the art. While replaceable blades (e.g., airplane propeller blades) are known in different fields, replaceable blades in a collapsible bag arrangement such as that of the present invention would not have been expected to have been found based upon knowledge in the art because such bags typically were used only for mixing media containing cells which, to avoid being lysed, must be stirred below a threshold of sheer, or for media containing other materials which can tolerate much higher sheer. In this aspect of the present invention, collapsible bag arrangements can be prepared with multiple blades and provided for use with either or both of two or more mixing profiles.

In one aspect, the impeller (in some embodiments, via magnetic coupling of the drive head to the impeller) is driven by a motor able to reverse its direction of rotation and/or to be finely tuned with respect to rotational speed. Reversal of direction of spin is not found or suggested by the known art but provides significant advantage as recognized by the present invention in terms of variety of aeration/sparger profiles, or the like. Fine tuning of impeller speed has been determined according to the present invention to allow for a precise and controllable degree and/or balance of aeration/sparging, sheer, or the like, which has been determined to be quite useful in connection with various media for mixture, especially those including cells. This embodiment of the invention allows for reproducible and controllable adjustment of rotational speed of the impeller that amounts of plus or minus 5% or less through a range of rotational speeds of between 10% and 90% of total maximum impeller rotational speed. In other embodiments, rotational tuning of 4%, 3%, 2%, or 1% of this speed is facilitated. In one arrangement, these aspects are realized by use of a servo motor.

In another aspect, the present invention includes a system that can reduce foam produced within a container or reduce the amount of foam contained in a head space of a container. In some cases, sensors and/or controllers may also be used to monitor and/or control foaming. As a specific, non-limiting example, a foam sensor may be inserted into a head space. In one embodiment, the foam sensor may include two or more foam probes with a voltage potential between them that is able to activate antifoaming (via a control system), for example, the addition of a chemical antifoaming agent, e.g., via a pump. In another embodiment, a foam sensor includes a first portion including a probe and a second portion including a wall of a reusable support structure (or a wall of a container) that can detect a change of electrical current flow between the probe and the wall (e.g., due to the presence of the foam). In another embodiment, a foam sensor uses an amperage draw of an external motor to detect foam in a container. In such an arrangement, the current may increase when the foam contacts an impeller driven by the motor. In yet another embodiment, the foam sensor can activate a mechanical antifoaming device via a control system. As another specific non-limiting example, mechanical foam control may be achieved, for example, via a mounting impeller in head of a container, turned upside down, optionally with fritted or non-fritted exhaust air exit elements to enhance foam breakage. Examples of impellers that can be used in an antifoaming system are described above in connection with FIGS. 4A-8.

More generally, in some embodiments, a device able to reduce or eliminate foam may be associated with a vessel, for example, within a container of the vessel. The antifoaming device may be able to reduce or eliminate foaming, for example, prior to foam accumulating in an exhaust or an outlet, plugging of filters, or the like. The antifoaming system may be run continuously, periodically, or in some cases, in response to certain events, e.g., within a bioreactor system and/or within the container. For example, the antifoaming device may include one or more sensors and a control system which is able to monitor foaming and act to reduce or eliminate the foaming.

In various embodiments, the antifoaming device may include a control system, which can include one or more foam sensors, for example, within a container. The foam sensor may be positioned in any place able to detect foaming and/or a consequence of foaming, for example, the alteration of pressure within an outlet of the container. For instance, a foam sensor may be positioned in a head space within the container, in an outlet port, in an exit line (e.g., in an exit air line, and/or upstream of an exit air filter), or the like. Detection of foam in one or more of the foam sensors may cause the control system to enact antifoam measures, as discussed below. In another set of embodiments, a sensor that detects foam or the effects of foam in a container may be a pressure sensor that detects overpressure (e.g., due to clogging by the foam), which may be used to determine the degree of foaming. For example, in one embodiment, foam detection may occur by a pressure sensor in a head space within a container, or within an outlet port.

Antifoaming techniques include, but are not limited to, a lowering of gas flow rate to the container and/or shut of gassing entirely, the addition of chemical antifoaming agents, which are known to those of ordinary skill in the art (e.g., via an external pump), a mechanical foam breaker mounted in head space, and/or the lowering or ceasing of an agitation rate of a mixer in the container.

In one set of embodiments, a mechanical antifoaming system is used to reduce or eliminate foaming. The mechanical antifoaming system can be positioned in any suitable location within the bioreactor system such as within the container. For instance, a mechanical antifoaming system may be fitted to the inside head space of a container of the present invention, or to an outlet port (which allows air and/or foam to exit the container). The mechanical antifoaming system may have any suitable structure able to reduce and/or eliminate foam. For instance, in one embodiment, the mechanical foam breaker includes one or more stainless steel plates or cones mounted on a hollow rotating shaft that penetrates the container. The shaft can be rotated by an external motor (e.g., a magnetically-operated motor) or other suitable apparatus. In some cases, a hollow motor shaft may be used, which may also provide a passage for gases exiting the container in some cases. In other cases, impellers such as the ones shown in FIGS. 4A-8 can be used.

In certain instances, a shaft associated with a mechanical antifoaming device is positioned between the inside and outside of the container. The location where the shaft exits the container may be maintained in a sterile condition. For instance, internal and/or external rotating seals may be used to maintain a sterile seal, and/or live hot steam may be used to facilitate maintenance of the sterile seal. By maintaining such a sterile seal, contamination caused by the shaft, e.g., from the external environment, from the exiting gases, etc., may be reduced or avoided.

Without wishing to be bound by any theory, it is believed that, as gas and/or foam passes through a mechanical antifoaming device, for example, between spinning impellers, plates or cones, a centrifugal force is applied to the foam which overcomes stabilizing surface tension forces and can result in collapse of the foam bubble. The fluid from the collapsed bubble may thus be ejected out and down to the container. Thus, the exiting gases may be at least substantially free of foam. The mechanical antifoaming device can be left running at all times or activated as needed via a sensor, e.g., via a sensor mounted in the head space of the container, as previously described.

Figure 7:
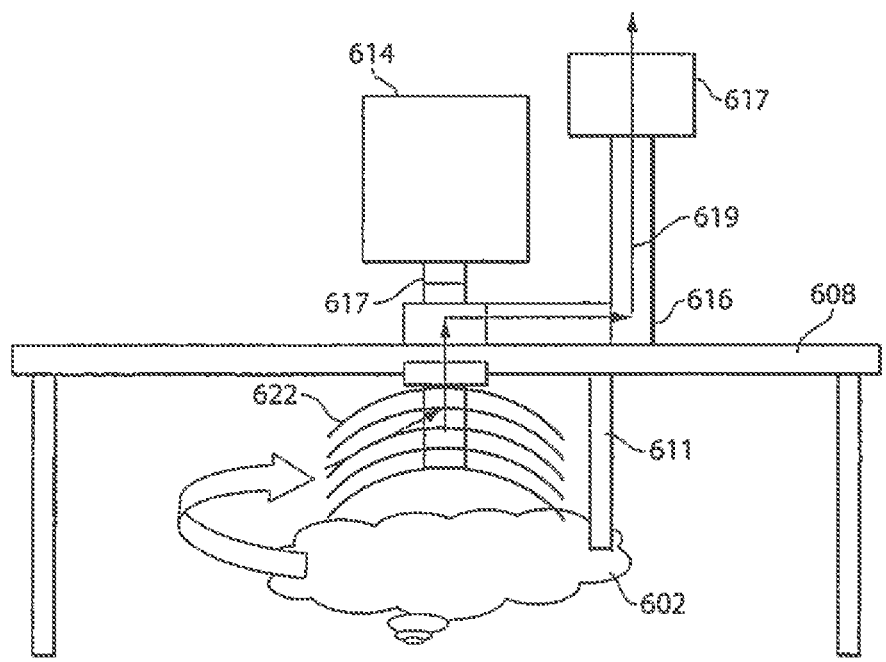
FIG. 7 shows an example of an antifoaming system, according to another embodiment of the invention.

Referring now to FIG. 7, one embodiment of such a mechanical antifoaming system is shown. In this figure, a foam 602 is produced, e.g., during a chemical, biochemical, and/or a biological reaction within a container 608 (e.g., a rigid container or a collapsible bag). In this example, foaming is detected by a foaming sensor 611 in electrical communication with a control system, which then causes an antifoaming device to activate. Here, the antifoaming device includes an external drive motor 614, which rotates a shaft 617 connected to vanes 622. Shaft 617 penetrates container 608 to reach its interior. The foam 602 is then disrupted as it is passed between spinning vanes 622. In addition, in this example, shaft 617 is hollow, and gases can pass through the shaft, exiting container 608, as indicated by arrows 619, passing through conduits 616 and optional filter 617.

In another embodiment, a mechanical antifoaming device of the invention does not penetrate the container. Thus, the mechanical antifoaming device may lack a rotating shaft or a hollow shaft, and/or may lack a seal. In addition, as there is no penetration of the container by such a mechanical antifoaming device, there may be no need to maintain the mechanical antifoaming device in a sterile condition, e.g., using internal and/or external rotating seals, live hot steam, or the like. Such a system may be formed, for instance, from steel, stainless steel or inexpensive hard plastic for installation in collapsible or disposable bags or other containers described herein.

Figure 8:
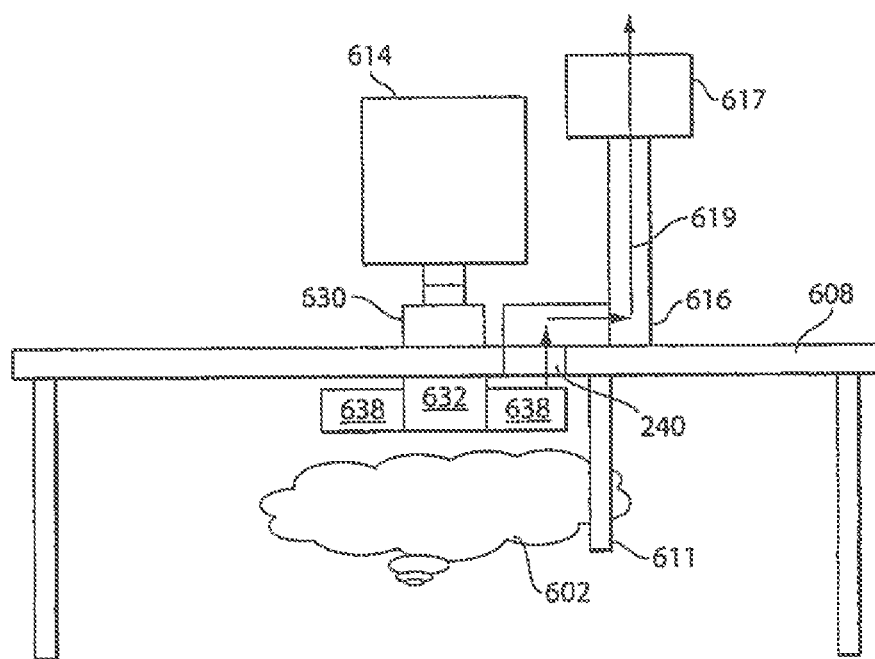
FIG. 8 shows another example of an antifoaming system, according to another embodiment of the invention.

Referring now to FIG. 8, a non-limiting example of such a mechanical antifoaming system is shown. In this figure, within container 608, foam 602 is produced, e.g., during a chemical and/or a biological reaction within the container. The foaming is detected by a foaming sensor 611, and a control system then causes an antifoaming device to activate. In this particular example, the antifoaming device includes an external drive motor 614, which includes a spinning external magnetic drive head 630. The lack of a penetrating shaft allows container 608 to be quickly removed from motor 614. Inside container 608, an internal magnetic hub 632 rotates as a result of the rotation of external magnetic drive head 632. This causes rotation of blades 638 attached to internal magnetic hub 632 (e.g., about a single axis), which then breaks down the foam. In this example, gases do not leave via a hollow shaft (as in FIG. 7), but instead pass through an outlet port 240 (which may be hollow, contain a porous frit element, etc.), exiting container 608, as indicated by arrows 619, passing through conduits 616 and filter 617.

Although FIGS. 7 and 8 show mechanical antifoaming devices that are positioned at or near a top portion of a container, in other embodiments, the devices can be positioned at any suitable location within a container, for example, near the center portion of a container. This can be achieved, for example, by extending the length of a shaft which supports an impeller, or by any other suitable configuration. The impeller can also be lowered or risen depending on the levels of liquid and foam in the container. Additionally, antifoaming devices may include more than one impeller in some instances. For example, a first impeller coupled to a shaft may be located near a top portion of the container and a second impeller coupled to the shaft may be positioned near the center of container. An antifoaming system of a vessel may be disposable or intended for a single use (e.g., along with the container), in some cases.

The impeller systems described herein may allow the system to mix fluids, solids, or foams of any type. For example, fluids inside the container may be mixed to provide distribution of nutrients and dissolved gases for cell growth applications. The same disposable container may be used for mixing buffers and media or other solutions in which a disposable product contact surface is desirable. This may also include applications in which the vessel is not required to be sterile or maintain sterility. Moreover, embodiments described herein enable the container holding the fluids/mixtures/gases to be removed and discarded from the reusable support structure such that the reusable support structure is not soiled by the fluids that are mixed in the container. Thus, the reusable support structure need not to be cleaned or sterilized after every use.

Another aspect of the invention includes multiple spargers (including sparging elements) that may be dimensioned for connection to different sources of gas and/or which may be independently controlled. The type of gas, number of spargers, and types and configurations of spargers used in a bioreactor system or a biochemical/chemical reaction system may depend, in part, on the particular process to be carried out (e.g., an aerobic versus anaerobic reaction), the removal of any toxic byproducts from the liquid, the control of pH of a reaction, etc. As described in more detail below in connection with certain embodiments described herein, a system may include separate spargers for different gases which may have different functions in carrying out, for example, a chemical, biochemical and/or biological reaction. For instance, a bioreactor system for cell cultivation may include different types of gases such as a "dissolved oxygen (DO) control gas" for controlling the amount of dissolved oxygen in the culture fluid, a "strip gas" for controlling the amount of toxic byproducts in the culture fluid, and a "pH control gas" for controlling the pH of the culture fluid. Each type of gas may be introduced into the culture using different spargers that can be independently operated and controlled. Advantageously, such a system may provide faster process control and less process control variability (compared to, for example, certain systems that combine a DO control gas, strip gas, and pH control gas into one gas stream introduced into a reactor). Chemical, biochemical and/or biological reactions carried out in bioreactor systems described herein may also require lower consumption of gas which can save money on expensive gases, and/or less total gas flow rate (e.g., for a strip gas), which can reduce foam generation and/or reduce the size of inlet gas sterile filters required.

In some embodiments, vessels described herein are a part of a bioreactor system. In bioreactors used for certain types of cell cultivation, cells may require nutrients such as sugars, a nitrogen source (such as ammonia ($NH_3$) or amino acids), various salts, trace metals and oxygen to grow and divide. Like the other nutrients, even and uniform distribution of oxygen throughout the reactor may be essential to provide uniform cell growth. Poor distribution of oxygen can create pockets of cells deprived of oxygen, leading to slower growth, alteration of the cell metabolism or even cell death. In certain applications where the cells are engineered to produce a bioproduct, oxygen deprivation can have a sever affect on the quantity and quality of bioproduct formation. The amount of nutrients available to cells at any one time depends in part on the nutrient concentration in the fluid. Sugars, nitrogen sources, salts, and trace metals may be soluble in fluid and, therefore, may be in excess and readily available to the cells. Oxygen, on the other hand, may be relatively poorly soluble or "dissolved" in water. In addition, the presence of salts plus the elevated temperature necessary to grow cells may further reduce dissolved oxygen concentration. To compensate, a rapid dissolved oxygen sensing system, constant and steady transfer of oxygen into the fluid (e.g., using one or more spargers as described herein), combined with rapid and even distribution in the bioreactor may be used to reduce or prevent oxygen starvation.

Since oxygen transfer from the gas bubbles entering the fluid of the culture may be an important control parameter, the time constant of responsiveness of the gas delivery system may also be important. In certain embodiments, as cell population density increases, the response rate of the gassing system to supply oxygen enriched DO control gas may become increasingly important. Accordingly, in some embodiments, systems described herein include one or more sensors such as a DO sensor which detects the need for more oxygen (or other gas), a gas controller, and one or more spargers which can be signaled to enrich the culture with extra oxygen using, for example, a $N_2/O_2/air$ control gas. Since delay time (e.g., several minutes) for this enriched gas to reach the reactor can result in a drop in DO which can lead to oxygen starvation, systems described herein may include a control feedback loop between the sensor(s), gas controller, and sparger(s). Thus, responsive, and even supply and distribution of oxygen-bearing control gas (e.g., a $N_2/O_2/air$ mix) may be provided for controlled, predictable cell growth and bioproduct formation. Systems described herein allowing independent control of spargers and/or gas compositions may be advantageous compared to systems that require gases to be flushed out before sparging a different gas into the container.

In addition, since compressed air and oxygen may be expensive to supply to the reactor, a system that provides just enough air enriched with just enough oxygen such that the bubbles are not lost to the head space of the container (and lost out through the exhaust line) may be implemented. This can be performed, for example, by controlling the amount and flow rate of a control gas independently of other gases used in the system (e.g., a strip gas and/or a pH control gas).

Without wishing to be bound by any theory, it is believed that the rate of oxygen transfer into the bioreactor fluid from air, pure oxygen or a gas mixture is directly related to the amount of total surface area of the bubbles in the fluid. Hence, larger bubbles provide less total surface area than a fine mist of very small bubbles. For this reason, in certain embodiments of the invention, a control gas may be provided through microporous spargers to create very small bubbles. A microporous sparger may include apertures having a size (e.g., average diameter) of, for example, less than less than 500 microns, less than 200 microns, less than 100 microns, less than 60 microns, less than 50 microns, less than 40 microns, less than 30 microns, less than 20 microns, less than 10 microns, less than 3 microns, less than about 1 micron, or less than 0.1 microns. In certain embodiments, microporous spargers have an aperture size between 0.1 and 100 microns. Of course, spargers having larger aperture sizes may also be used. For instance, a sparger may have an aperture size between 0.1 and 10 mm. The aperture size may be greater than 100 microns, greater than 200 microns, greater than 500 microns, greater than 1 mm, greater than 3 mm, greater than 5 mm, greater than 7 mm, or greater than 10 mm. The aperture may have any suitable cross-sectional shape (e.g., circular, oval, triangular, irregular, square or rectangular, or the like). Spargers having combinations of aperture sizes can be incorporated into vessels described herein.

Additionally, good cell growth and controlled metabolism may be dependent upon removal of toxic byproducts of cell growth, such as, for example, carbon dioxide, ammonia and volatile organic acids. Carbon dioxide may be highly soluble in water, which can exacerbate its toxic effect on cells. These byproducts can be "stripped" out of the culture fluid by gassing the culture using a strip gas. Accordingly, even distribution of strip gas and strip gas that is introduced at a flow rate sufficiently high enough for bubbles to escape out of the culture (and out the exhaust vent, for example) may be important for cell growth and/or bioproduct production. These parameters may be controlled independently of other gases used in the system (e.g., a control gas and/or a pH control gas) using a separate sparger for the strip gas.

In some instances, a strip gas is introduced into a container using a sparger having an aperture size between 0.1 and 10 mm. For example, the aperture size may be greater than 100 microns, greater than 200 microns, greater than 500 microns, greater than 1 mm, greater than 3 mm, greater than 5 mm, greater than 7 mm, or greater than 10 mm. These aperture sizes can allow relatively larger bubbles to pass through the liquid of the container, which can strip any toxic byproducts out of the liquid without creating large amounts of foam in the head space of the container.

In certain embodiments, a pH control gas is used to control the pH of the fluid in a bioreactor system. For example, carbon dioxide may be used to increase solution pH and ammonia may be used to decrease solution pH. In one embodiment, a pH control gas may include a combination of carbon dioxide, ammonia, or other gases to control (e.g., increase or decrease) pH. In another embodiment, the pH of a reaction fluid is controlled by a first sparger containing an agent that increases pH (e.g., $CO_2$) and a second sparger containing an agent that decreases pH (e.g., $NH_3$).

One or more pH control gases may be added to a container of the bioreactor system upon signals from a pH control sensor associated with the system. The pH control gases may be operated independently and without interference by oxygen demand (e.g., a DO control gas) or strip gas systems. A pH control gas may be introduced into a container using spargers having apertures of various sizes.

In other embodiments, cells that are normally grown without oxygen (e.g., anaerobic reactions) or which are even sensitive to oxygen require removal of oxygen from the culture. Even and controlled distribution of nitrogen gas in these cultures may be used to control proper cell growth and product formation.

As mentioned, in some embodiments of the present invention, gases such as air, $CO_2$, $O_2$, $N_2$, $NH_3$, and/or dissolved oxygen may be sparged into the container. In some cases, the sparging can be controlled, for instance, such that the sparging can be rapidly activated or altered as needed. Multiple spargers may be used in some cases. For example, in one embodiment, different gas compositions may each be introduced into the container using multiple spargers, e.g., a first sparger for a first gas composition, a second sparger for a second gas composition, a third sparger for a third gas composition, etc. The gases may differ in composition and/or in concentration. As a specific example, a first gas composition may include air with 5% $CO_2$, and a second gas composition may include air with 10% $CO_2$; in another example, a first gas composition may include $O_2$, and a second gas composition may include $N_2$; in yet another example, a first gas composition may include a control gas, a second gas composition may include a strip gas, and a third gas composition may include a pH control gas. Of course, other combinations of gases are also possible. In some cases, multiple spargers may be useful to allow faster responses, e.g., as the gas composition being introduced into the container may be rapidly changed by activating different spargers, e.g., singly and/or in combination. As a specific example, the gas being introduced into a container can be rapidly switched from a first gas (via a first sparger) to a second gas (via a second sparger), and/or to a combination of the first and second gas, or a combination of the second gas and a third gas, etc. The flow rates of each gas can also be changed independently of one another. (In contrast, with a single sparger, a change in composition requires that the new composition reach the sparger before being introduced into the container.) Moreover, the use of multiple spargers can allow customization of the type of sparger for a particular type of gas, e.g., a strip gas, DO control gas, pH control gas, air, $CO_2$, $O_2$, $N_2$, $NH_3$, or any other suitable gas, if desired.

Sparging may be run continuously, periodically, or in some cases, in response to certain events, e.g., within a bioreactor system and/or within the container. For example, as mentioned, the spargers may be connected to one or more sensors and a control system which is able to monitor the amount of sparging, the degree of foaming, the amount or concentration of a substance in the container, and respond by initiating, reducing, or increasing the degree of sparging of one or more composition(s) of gases.

In one particular embodiment, a vessel (e.g., as part of a reactor system for performing a biological, biochemical or chemical reaction) is configured to contain a volume of liquid and includes a container (e.g., a collapsible bag) having a volume of at least 2 liters (or any other suitable volume) to contain the volume of the liquid. The vessel may optionally include a support structure for surrounding and containing the container. Additionally, the vessel includes a first sparger connected or dimensioned to be connected to a source of a first gas composition in fluid communication with the container, and a second sparger connected or dimensioned to be connected to a source of a second gas composition different from the first gas composition in fluid communication with the container. The vessel further comprises a control system operatively associated with the first and second spargers and configured to operate the spargers independently of each other. Of course, third, fourth, fifth, or greater numbers of spargers can be included (e.g., greater than 10, or greater than 20 spargers), depending on, for example, the size of the container. In some embodiments, the vessel further comprises a mixing system including an impeller and a base plate, wherein the first and/or second spargers is associated with the base plate. In one particular embodiment, the first gas composition comprises air and the second gas composition comprises air supplemented with $O_2$ and $N_2$. If additional spargers are included, the spargers can be connected to a source of gas comprising $N_2$, $CO_2$, $NH_3$ and/or any other suitable gas.

In another exemplary embodiment, a vessel configured to contain a volume of liquid comprises a container (e.g., a collapsible bag) to contain the liquid, and optionally, a support structure for surrounding and containing the collapsible bag. The vessel includes a first sparger connected to the container, the first sparger having a first aperture size, wherein at least a portion of the first sparger is dimensioned to be connected to a source of a first gas composition. The vessel also includes a second sparger connected to the container, the second sparger having a second aperture size, wherein at least a portion of the second sparger is dimensioned to be connected to a source of a second gas composition. The second gas composition may have the same or a different composition than the first gas composition. In some embodiments, the vessel is part of a bioreactor system; or, the vessel may be a part of a biochemical/chemical reaction system, or a mixing system. The vessel may include a control system operatively associated with the first and second spargers and may be configured to operate the spargers (or gases associated therewith) independently of each other. The vessel may include any suitable number of spargers (e.g., greater than 10 or greater than 20 spargers), and the container may have any suitable volume (e.g., at least 2, 10, 20, 40, or 100 liters). The first and/or second gas composition(s) may include, for example, $N_2$, $O_2$, $CO_2$, $NH_3$, or air. For example, in one instance, the first gas comprises air and the second gas comprises air supplemented with $O_2$ and $N_2$. The first aperture size may be larger than the second aperture size. For instance, the first aperture size may be between 0.1 and 10 mm, and the second aperture size may be between 0.1 and 100 microns.

Apertures associated with spargers can be formed in any suitable material. For instance, in one embodiment, a porous polymeric material is used as a sparging element to allow transport of gas from one side to another side of the material. Apertures can also be formed in other materials such as metals, ceramics, polymers, and/or combinations thereof. Materials having pores or apertures can have any suitable configuration. For example, the materials may be knitted, woven, or used to form meshes or other porous elements. The elements may be in the form of sheets, films, and blocks, for example, and may have any suitable dimension. In some cases, such elements are incorporated with impellers or impeller supports, e.g., as illustrated in FIG. 5. The elements can be positioned and held within regions of the impeller or impeller support securely enough for suitable use and accordance with the invention by any number of techniques including, for example, friction fitting, press fitting, detent mechanism, a clipping and clip release arrangement, fastening with screws, pegs, clamps, or the like, welding (e.g., heat and ultrasonic welding), and use of adhesives. In other embodiments, portions of the impeller and/or impeller support can be fabricated directly with pores or apertures that can allow fluids to flow therethrough.

The vessel may optionally include one or more sensors in electrical communication with the control system for determining an amount or concentration of a gas (e.g., $O_2$, $N_2$, $CO_2$, $NH_3$, a bi-product of a reaction) in the container. Additionally and/or alternatively, the vessel may include a sensor in electrical communication with the control system for determining a pH of a liquid in the container, or an amount or level of a foam in the bag.

Figure 9:
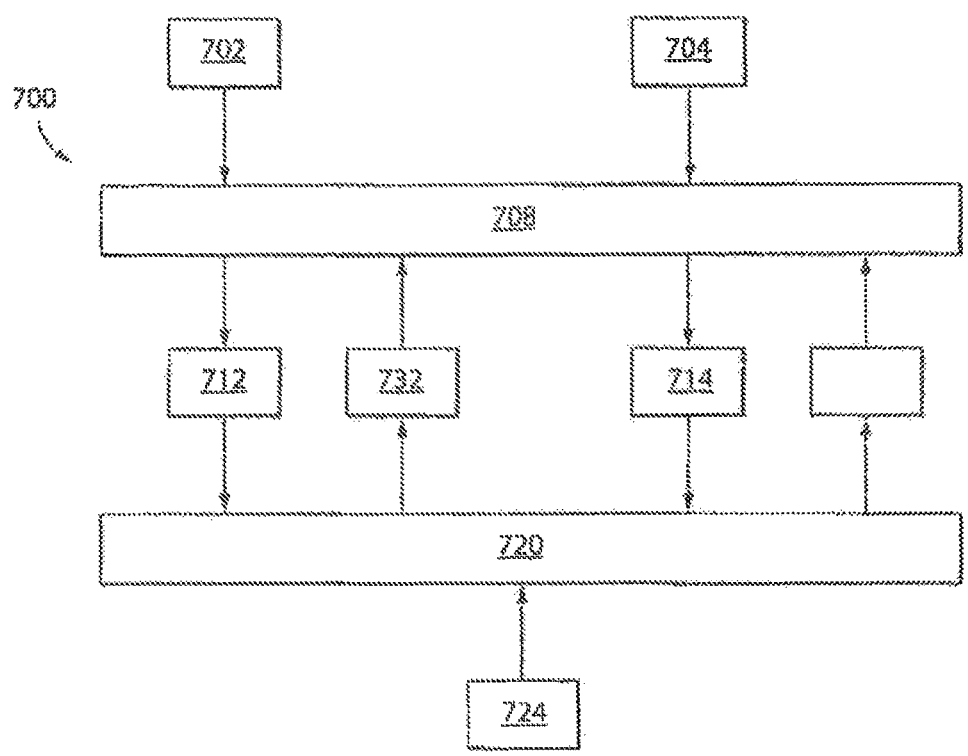
FIG. 9 shows an example of a control and feedback process, according to another embodiment of the invention.

As mentioned, control systems and feedback loops may be used to control the degree of sparging in one embodiment, or degree of mixing, or activity of an antifoaming system in other embodiments. One example of such a control and feedback process is shown in the embodiment illustrated in FIG. 9. System 700 may include a first sensor 702 (e.g., for detecting the amount and/or concentration of $CO_2$ of a liquid in the container) and a second sensor 704 (e.g., for detecting the amount and/or concentration of $O_2$ of a liquid in the container). After calibrating the sensors, reagents may be added to a container 708 and a fluidic manipulation process, such as mixing or performing a biological, chemical, or biochemical reaction, may be take place. The amount of a gas such as $O_2$ and $CO_2$ may vary in the liquid of the container as the process proceeds. For example, if a biological reaction involving cells takes place, the cells may consume $O_2$ and form $CO_2$ over time, which may vary depending on the growth stage of the cells. Thus, the amount and/or concentration of gases can be determined by the sensors (e.g., as a function of time), and signals 712 and 714 related to the amounts and/or concentrations of the gases can be sent to a control system 720. The control system may include recorded parameters 724, such as threshold levels of one or more gases that can inputted by a user prior to or during the reaction. For example, a parameter may include a certain threshold level of $CO_2$ in the liquid before a sparger is activated to reduce the amount of $CO_2$ using a strip gas. Accordingly, a signal may be sent from the control system to activate a component 732, such as a valve connected to a source of a strip gas used to reduce the amount of $CO_2$. As the strip gas is introduced into container 708, the amount and/or concentration of $CO_2$ may decrease, which can be measured by 712 and signals sent to the control system. When the amount and/or concentration of $CO_2$ decreases to a certain level, the control system can lower or deactivate the amount of $CO_2$ being introduced into the container, thereby completing the feedback loop. A similar process can take place independently of the process described above using second sensor 714, which may measure, for example, a second gas, a pH, or an amount of a foam in a head space of the container.

In another aspect, a bubble column or airlift system (utilizing bubbles of air or other gas) may be used with the disposable bioreactor bag. Such a system may provide a mixing force by the addition of gas (e.g., air) near the bottom of the reactor. Here, the rising gas bubble and the lower density of gas-saturated liquid rise, displacing gas-poor liquid which falls, providing top-to-bottom circulation. The path of rising liquid can be guided, for example, using dividers inside the chamber of the bag. For instance, using a sheet of plastic which bisects the interior of the bioreactor bag, e.g., vertically, with a gap at the top and the bottom. Gas may be added on one side of the divider, causing the gas and gas-rich liquid to rise on one side, cross over the top of the barrier sheet, and descend on the other side, passing under the divider to return to the gas-addition point. In addition, such a bubble column/air-lift mixing system and method may be combined with any of the other mixing systems described herein.

In one aspect, a bioreactor system as described herein includes an enclosed resin loading/column packing system. Typically, column packing typically may be accomplished in a clean room with open carboys containing the resin which is manually mixed while the resin slurry is pumped onto the column. In one embodiment, however, a container such as a flexible container is loaded with chromatography resin which is slurried by an agitator while the slurry is pumped into a column.

In certain chemical, biochemical and/or biological processes requiring light, a bioreactor system described herein may include direct, indirect and/or piped-in lighting, e.g., using fiber-optics, according to another aspect of the invention. Any suitable light source may be used. Such bioreactor systems may be useful for processing, for example, plant cells, e.g., to activate photosynthesis. In one particular embodiment, a phosphorescent flexible container is used to provide light, e.g., for growth of plant cells.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. A bioreactor comprising:
   a collapsible bag configured to be received in a reusable rigid support structure, the collapsible bag having an interior configured to receive a volume of liquid, the collapsible bag including an impeller support having a rotatable impeller;
   a first sparger connected to the collapsible bag, the first sparger having a port configured for attachment to tubing in fluid communication with a source of gas; and
   a second sparger connected to the collapsible bag, the second sparger having a port configured for attachment to tubing in fluid communication with a source of gas;
   wherein the first and second spargers are formed in the impeller support of the collapsible bag;
   wherein the first sparger has a first aperture size, and wherein the second sparger has a second aperture size that is different from the first aperture size;
   wherein the impeller support has a first portion configured to receive and/or support a shaft of the impeller and a second portion adjacent to the first portion, the second portion being thinner than the first portion; and
   wherein the first sparger and second sparger are formed in the first portion of the impeller support.

2. The bioreactor of claim 1 wherein the first portion has a size that is substantially the same as a diameter of the impeller.

3. The bioreactor of claim 1, further comprising:
   a control system operatively associated with the first and second spargers and configured to operate the first and second spargers independently of each other.

4. The bioreactor of claim 1, wherein the vessel comprises greater than 10 spargers, each connected to the collapsible bag.

5. The bioreactor of claim 1, wherein the vessel comprises greater than 20 spargers, each connected to the collapsible bag.

6. The bioreactor of claim 1, wherein collapsible bag has a volume of at least 2 liters.

7. The bioreactor of claim 1, wherein the first sparger and/or the second sparger are in fluid communication with a source of $N_2$, $O_2$, $CO_2$, $NH_3$, and/or air.

8. The bioreactor of claim 7, wherein the first sparger is in fluid communication with a source of a gas comprising air and the second sparger is in fluid communication with a source of a gas comprising air supplemented with $O_2$ and/or $N_2$.

9. The bioreactor of claim 1, wherein first aperture size is larger than the second aperture size.

10. The bioreactor of claim 1, wherein the first aperture size is between 0.1 mm and 10 mm.

11. The bioreactor of claim 1, wherein the first aperture size is between 100 microns and 10 mm.

12. The bioreactor of claim 1, wherein the first aperture size is between 500 microns and 3 mm.

13. The bioreactor of claim 1, wherein the first aperture size is between 500 microns and 1 mm.

14. The bioreactor of claim 1, wherein the second aperture size is between 0.1 microns and 200 microns.

15. The bioreactor of claim 1, wherein the second aperture size is between 0.1 microns and 100 microns.

16. The bioreactor of claim 1, wherein the second aperture size is between 0.1 microns and 50 microns.

17. The bioreactor of claim 1, wherein the second aperture size is between 100 microns and 200 microns.

18. The bioreactor of claim 1, wherein:
   the first sparger and the second sparger are connected to a bottom of the collapsible bag.

19. The bioreactor of claim 1, wherein:
   the first and second spargers each include tubing configured for fluid communication with the source of gas and a sparging element having a plurality of apertures.

20. The bioreactor of claim 1, wherein the collapsible bag is configured to receive a sensor.

* * * * *